United States Patent
Wilsey

(10) Patent No.: US 10,408,784 B2
(45) Date of Patent: *Sep. 10, 2019

(54) DETERMINING BLOOD GLUCOSE IN A SMALL VOLUME SAMPLE RECEIVING CAVITY AND IN A SHORT TIME PERIOD

(71) Applicants: Roche Diabetes Care, Inc., Indianapolis, IN (US); Roche Operations Ltd., Hamilton (BM)

(72) Inventor: Christopher D. Wilsey, Carmel, IN (US)

(73) Assignees: Roche Diabetes Care, Inc., Indianapolis, IN (US); Roche Operations Ltd., Hamilton (BM)

(*) Notice: Subject to any disclaimer, the term of this patent is extended or adjusted under 35 U.S.C. 154(b) by 0 days.

This patent is subject to a terminal disclaimer.

(21) Appl. No.: 15/584,660

(22) Filed: May 2, 2017

(65) Prior Publication Data

US 2017/0328858 A1 Nov. 16, 2017

Related U.S. Application Data

(63) Continuation of application No. 14/695,528, filed on Apr. 24, 2015, now Pat. No. 9,638,658, which is a continuation of application No. 13/929,293, filed on Jun. 27, 2013, now Pat. No. 9,017,544, which is a continuation of application No. 13/719,967, filed on Dec. 19, 2012, now abandoned, which is a continuation of application No. 13/433,779, filed on
(Continued)

(51) Int. Cl.
*G01N 27/327* (2006.01)
*C12Q 1/00* (2006.01)

(52) U.S. Cl.
CPC ........ *G01N 27/3275* (2013.01); *C12Q 1/006* (2013.01); *G01N 27/3272* (2013.01)

(58) Field of Classification Search
CPC ............. G01N 27/327; G01N 27/3271; G01N 27/3272

See application file for complete search history.

(56) References Cited

U.S. PATENT DOCUMENTS

| 4,184,751 A | 1/1980 | Nicholson |
| 4,759,828 A | 7/1988 | Young et al. |

(Continued)

FOREIGN PATENT DOCUMENTS

| EP | 0 170 375 A2 | 2/1986 |
| EP | 2 206 218 A2 | 12/1986 |

(Continued)

OTHER PUBLICATIONS

Ulla Wollenberger, "Electrochemical Biosensors—Ways to Improve Sensor Performance," Biotechnology and Genetic Engineering Reviews—vol. 13, Dec. 1995 (Year: 1995).*

(Continued)

*Primary Examiner* — Alexander S Noguerola
(74) *Attorney, Agent, or Firm* — Woodard, Emhardt, Henry, Reeves & Wagner, LLP

(57) ABSTRACT

The concentration of glucose in a blood sample is determined by methods utilizing test strips having a sample receiving cavity having a volume from about 0.3 µl to less than 1 µl and determining the glucose concentration within a time period from about 3.5 seconds to about 8 seconds.

4 Claims, 13 Drawing Sheets

Related U.S. Application Data

Mar. 29, 2012, now Pat. No. 8,349,168, which is a continuation of application No. 13/339,598, filed on Dec. 29, 2011, now Pat. No. 8,303,801, which is a continuation of application No. 12/477,239, filed on Jun. 3, 2009, now abandoned, which is a continuation of application No. 11/677,737, filed on Feb. 22, 2007, now abandoned, which is a continuation of application No. 10/382,322, filed on Mar. 5, 2003, now Pat. No. 7,276,147, which is a continuation-in-part of application No. 10/264,785, filed on Oct. 4, 2002, now abandoned, said application No. 11/677,737 is a continuation-in-part of application No. 10/264,891, filed on Oct. 4, 2002, now Pat. No. 7,276,146.

(56) References Cited

U.S. PATENT DOCUMENTS

| | | |
|---|---|---|
| 4,832,814 A | 5/1989 | Root |
| 5,049,487 A | 9/1991 | Phillips et al. |
| 5,120,420 A | 6/1992 | Nankai et al. |
| 5,192,415 A | 3/1993 | Yoshioka et al. |
| 5,202,261 A | 4/1993 | Musho et al. |
| 5,250,439 A | 10/1993 | Musho et al. |
| 5,262,305 A | 11/1993 | Heller et al. |
| 5,264,103 A | 11/1993 | Yoshioka et al. |
| 5,282,950 A | 2/1994 | Dietze et al. |
| 5,288,636 A | 2/1994 | Pollmann et al. |
| 5,352,351 A | 10/1994 | White et al. |
| 5,354,447 A | 10/1994 | Uenoyama et al. |
| 5,389,215 A | 2/1995 | Horiuchi et al. |
| 5,437,772 A | 8/1995 | De Castro et al. |
| 5,437,999 A | 8/1995 | Diebold |
| 5,508,171 A | 4/1996 | Walling et al. |
| 5,509,410 A | 4/1996 | Hill et al. |
| 5,565,085 A | 10/1996 | Ikeda et al. |
| 5,575,895 A | 11/1996 | Ikeda et al. |
| 5,582,697 A | 12/1996 | Ikeda et al. |
| 5,611,900 A | 3/1997 | Worden et al. |
| 5,650,062 A | 7/1997 | Ikeda et al. |
| 5,658,443 A | 8/1997 | Yamamoto et al. |
| 5,670,031 A | 9/1997 | Hintsche et al. |
| 5,698,083 A | 12/1997 | Glass |
| 5,707,502 A | 1/1998 | McCaffrey et al. |
| 5,708,247 A | 1/1998 | McAleer et al. |
| 5,720,862 A | 2/1998 | Hamamoto et al. |
| 5,723,345 A | 3/1998 | Yamauchi et al. |
| 5,762,770 A | 6/1998 | Pritchard et al. |
| 5,820,551 A | 10/1998 | Hill et al. |
| 5,858,691 A | 1/1999 | Hoenes et al. |
| 5,863,400 A | 1/1999 | Drummond et al. |
| 6,004,441 A | 12/1999 | Fujiwara et al. |
| 6,042,714 A | 3/2000 | Lin et al. |
| 6,103,509 A | 8/2000 | Sode |
| 6,120,676 A | 9/2000 | Heller et al. |
| 6,125,292 A | 9/2000 | Uenoyama et al. |
| 6,143,164 A | 11/2000 | Heller et al. |
| 6,153,069 A | 11/2000 | Pottgen et al. |
| RE36,991 E | 12/2000 | Yamamoto et al. |
| 6,156,173 A | 12/2000 | Gotoh et al. |
| 6,193,873 B1 | 2/2001 | Ohara et al. |
| 6,212,417 B1 | 4/2001 | Ikeda et al. |
| 6,241,862 B1 | 6/2001 | McAleer et al. |
| 6,258,229 B1 | 7/2001 | Winarta et al. |
| 6,270,637 B1 | 8/2001 | Crismore et al. |
| 6,284,125 B1 | 9/2001 | Hodges et al. |
| 6,299,757 B1 | 10/2001 | Feldman et al. |
| 6,338,790 B1 | 1/2002 | Feldman et al. |
| 6,475,372 B1 | 11/2002 | Ohara et al. |
| 6,531,040 B2 | 3/2003 | Muscho et al. |
| 6,576,117 B1 | 6/2003 | Iketaki et al. |
| 6,582,573 B2 | 6/2003 | Douglas et al. |
| 6,592,745 B1 | 7/2003 | Feldman et al. |
| 6,662,439 B1* | 12/2003 | Bhullar ............... G01N 27/3272 204/294 |
| 6,736,957 B1 | 5/2004 | Forrow et al. |
| 6,890,421 B2 | 5/2005 | Ohara et al. |
| 7,276,146 B2 | 10/2007 | Wilsey |
| 7,276,147 B2 | 10/2007 | Wilsey |
| 8,298,401 B2 | 10/2012 | Wilsey |
| 8,329,026 B2 | 12/2012 | Wilsey |
| 8,349,168 B2 | 1/2013 | Wilsey |
| 8,425,759 B2 | 4/2013 | Wilsey |
| 9,017,543 B2 | 4/2015 | Wilsey |
| 2002/0092612 A1* | 7/2002 | Davies ................ C12Q 1/001 156/292 |
| 2003/0217918 A1 | 11/2003 | Davies et al. |
| 2005/0176153 A1 | 8/2005 | Ohara et al. |
| 2010/0012517 A1 | 1/2010 | Feldman et al. |
| 2010/0295373 A1 | 11/2010 | Eisenring |

FOREIGN PATENT DOCUMENTS

| | | |
|---|---|---|
| EP | 0 859 230 A1 | 8/1988 |
| EP | 0 359 831 | 3/1990 |
| EP | 0 467 219 B1 | 1/1992 |
| EP | 0 924 520 A2 | 6/1999 |
| EP | 0 585 113 | 12/1999 |
| EP | 0 964 059 A2 | 12/1999 |
| EP | 1 067 384 A2 | 1/2001 |
| EP | 1 119 637 B1 | 8/2001 |
| EP | 1 195 441 | 4/2002 |
| EP | 1 252 514 B1 | 10/2002 |
| EP | 1 259 173 B1 | 8/2005 |
| JP | 1994/22793 | 7/1990 |
| JP | 05312761 A1 | 11/1993 |
| JP | H05-312761 A1 | 11/1993 |
| JP | 1996/320304 | 3/1995 |
| JP | 1997/159644 | 6/1997 |
| JP | H10-002874 A1 | 1/1998 |
| JP | 11-064271 A | 3/1999 |
| JP | 1194790 | 4/1999 |
| JP | 1194791 A1 | 4/1999 |
| JP | 11108879 A1 | 4/1999 |
| JP | H11-094790 A1 | 4/1999 |
| JP | H11-094791 A1 | 4/1999 |
| JP | H11-108879 A1 | 4/1999 |
| JP | 11125618 A1 | 5/1999 |
| JP | H11-125618 A1 | 5/1999 |
| JP | 2000/116626 | 4/2000 |
| JP | 2000/258382 | 9/2000 |
| JP | 11064271 A | 2/2014 |
| WO | WO 1986/07632 A1 | 12/1986 |
| WO | WO 89/09259 | 10/1989 |
| WO | WO 1995/22597 | 8/1995 |
| WO | WO 1995/28634 A1 | 10/1995 |
| WO | WO 1997/00441 A1 | 1/1997 |
| WO | WO 1997/18465 A1 | 5/1997 |
| WO | WO 1997/12242 | 8/1997 |
| WO | WO 1997/30344 | 8/1997 |
| WO | WO 1998/35225 A1 | 8/1998 |
| WO | WO 1999/17115 A1 | 4/1999 |
| WO | WO 1999/45387 | 9/1999 |
| WO | WO 2000/20626 | 4/2000 |
| WO | WO 2000/42422 A1 | 7/2000 |
| WO | WO 2000/73778 | 12/2000 |
| WO | WO 2001/25775 A1 | 4/2001 |
| WO | WO 2001/33216 | 5/2001 |
| WO | WO 2001/41643 | 6/2001 |
| WO | WO 2001/57510 A2 | 8/2001 |
| WO | WO 2001/57510 A2 | 8/2001 |
| WO | WO 2001/67099 A1 | 9/2001 |
| WO | WO 2001/73124 A2 | 10/2001 |

OTHER PUBLICATIONS

English Abstract of JP 1994-022793.
English Abstract of JP 1996-320304.
"Quick Start Guide" for the OneTouch® Ultra™ Blood Glucose Monitoring System.
"Request for Ex Parte Reexaminatio by Third Party Requestor," filed against U.S. Pat. No. 7,276,146, with appendix.

(56) References Cited

OTHER PUBLICATIONS

"Request for Ex Parte Reexamination by Third Party Requestor," filed against U.S. Pat. No. 7,276,147, with appendix.
*Roche Diagnostics Operations, Inc. et al.* v. *Abbott Diabetes Care, Inc. et al.*, CA No. 07-753; Memorandum Opinion dated Sep. 15, 2009.
*Roche Diagnostics Operations, Inc. et al.* v. *Abbott Diabetes Care, Inc. et al.*, CA No. 07-753; Order dated Sep. 15, 2009.
*Roche Diagnostics Operations, Inc. et al.* v. *Diagnostic Devices, Inc. et al.*, CA No. 07-753-JJF, Roche's Motion for Reconsideration of Claim Construction Imposing an Approximately 100 μm Limit on Width of "Microelectrode", Feb. 14, 2011.
*Roche Diagnostics Operations, Inc. et al.* v. *Abbott Diabetes Care, Inc. et al.*, CA No. 07-753; Defendant's Response to Roche's Motion for Reconsideration Oct. 21, 2009.
*Roche Diagnostics Operations, Inc. et al.* v. *Diagnostic Devices, Inc. et al.*, CA No. 07-753-JJF, Roche's Motion for Leave to File Reply in Support of Request for Reconsideration of Claim Construction of "Electrode" Oct. 21, 2009.
*Roche Diagnostics Operations, Inc. et al.* v. *Diagnostic Devices, Inc. et al*, C.A. No. 07-753-JJF, Roche's Invited comments to the court's Tentative Ruling Denying Reconsideration of Claim Construction Order; Feb. 15, 2011.
*Roche Diagnostics Operations, Inc. et al.* v. *Lifescan, Incorporated et al.*, Appeal from U.S. District Court for the District of Delaware, No. 07-CV-0753; Replacement Brief of appellants Roche Diagnostics Operations, Inc. and Corange International Limited; Oct. 18, 2010.
*Roche Diagnostics Operations, Inc. et al.* v. *Lifescan, Incorporated et al.*, Appeal from U.S. District Court for the District of Delaware, No. 07-CV-0753; Non-Confidential Brief for Defendant-Appellee Lifescan, Incorporated, Dec. 22, 2010.
*Roche Diagnostics Operations, Inc. et al.* v. *Lifescan, Incorporated et al.*, Appeal from U.S. District Court for the District of Delaware, No. 07-CV-0753; Amended Brief of Defendant Cross Appellant Nova Biomedical Corporation; Mar. 25, 2011.
*Roche Diagnostics Operations, Inc. et al.* v. *Lifescan, Incorporated et al.*, Appeal from U.S. District Court for the District of Delaware, No. 07-CV-0753; Replacement Brief of Appellants Roche Diagnostics Operations, Inc. and Corange International Limited; May 6, 2011.
*Roche Diagnostics Operations, Inc. et al.* v. *Lifescan Inc. and Nova Biomedical Corp.*, Appeal from U.S. District Court for the District of Delaware 07-CV-0753, decision dated Jan. 25, 2012.
*Abbott* v. *Roche 01* —Abbott's Complaint, Aug. 1, 2005.
*Abbott* v. *Roche 03* —Abbott's Complaint, Oct. 4, 2005.
*Abbott* v. *Roche 08* —Abbott's Initial Markman Brief, Dec. 1, 2006.
Answer, Affirmative Defenses and Counterclaims, Defendant Nova Biomedical Corporation, C.A. No. 07-753 JJF, filed Jan. 11, 2008.
Aoki et al., "Time-Dependence of Diffusion-Controlled Currents of a Soluble Redox Couple at Interdigitated Microarray Electrodes," J. Electroanal. Chem. 266 (1989) 11-20.
Aoki, Hoichi et al.; Quantitative Analysis of Reversible Diffusion-Controlled Currents of Redox Soluble Species at Interdigitated Array Electrodes Under Steady-State Conditions, J. Electroanal. Chem.; 1988; 269-282, 256; The Netherlands.
Bartlett, P.N. and Whitaker, R.G., "Electrochemical Immobilisation of Enzymes: Part II. Glucose Oxidase Immobilised in Poly-N-Methylpyrrole", J. Electroanal. Chem. 224 (1987) 37-48.
Bartlett, P.N. and Whitaker, R.G., "Electrochemical Immobilisation of Enzymes: Part I, Theory", J. Electroanal. Chem., 224 (1987) 27-35.
*Bayer* v. *Roche 01*—Roche's Opening Claim Construction Brief, pp. 1-8 and 36-70, Nov. 13, 2009.
*Bayer* v. *Roche 02*—Ruling on Claim Construction, pp. 1-8 and 27, Apr. 27, 2010.
*Bayer* v. *Roche 03*—Bayer's Pre-Hearing Brief, pp. 19-27 and 43-48.
*Bayer* v. *Roche 04*—Roche's Post-Hearing Brief, pp. 1-3 and 74-112.
*Bayer* v. *Roche 05*—Bayer's Response to Roche's Post-Hearing Brief, pp. VI-1 through VIII-33.
*Bayer* v. *Roche 06*—Final Award, Mar. 30, 2011, pp. 34-52.
*Bayer* v. *Roche 07*—ALCM Meeting, TX-361, Aug. 21-23, 2000, 50 pages.
*Bayer* v. *Roche 07*—PPQ Study, TX-324.
*Bayer* v. *Roche 08*—OTU Chart, TX-600, 2 pages.
*Bayer* v. *Roche 09*—Morgan Email, TX-691, 18 pages.
*Bayer* v. *Roche 10*—OTU Report, TX-727, 52 pages.
*Bayer* v. *Roche 11*—Bayer's Responsive Appeal Brief, pp. 90-108.
*Bayer* v. *Roche 12*—Roche's Responsive Appeal Brief.
Burke, David W. and Surridge, Nigel A., "Improved-Accuracy Biosensor Strip for Accu-Chek™ Advantage ®", presented orally at ACS Boston Meeting (-1993-1994).
Chen et al, ("β-Cyclodextrin cation exchange polymer membrane for improved second-generation glucose biosensor," Analytica Chimca Acta 306 (1995) 201-208.
Chiba, K.; Ohsaka, T.; Ohnuki, Y.; and Oyama, N., "Electrochemical Preparation of a Ladder Polymer Containing Phenazine Rings", J. Electroanal. Chem., 219 (1987) 117-124.
Legal Action before Intellectual Property High Court against Japanese Trial No. 19718/2008. Case No. (Gyo-ke) 10174/2010 (Japanese Patent Application No. 546093/2003) Plaintiff: F. Hoffmann-La Roche AG.
Defendant Bayer Healthcare, LLC's Answer and Affirmative Defenses to Complaint for Patent Infringment, Civil Action No. 07-753-JJF, filed Jan. 11, 2008.
Depuy et al., "Quantitative Analysis of Aqueous Solutions by FTIR Sectroscopy of Dry-Extract", SPIE, 1991, vol./Issue No. 1575, pp. 501-502, The Society of Photo-Optical Instrumentation Engin.
Enclosures A, B, C1, C2, C3, and C4 of Opposition Brief Against European Patent 1 269 173 by Roche Diagnostics GmbH, May 16, 2006—TheraSense FreeStyle blood glucose monitoring system; prior public use and documentation abouts this earlier product May 16, 2006.
English Abstract for JP1997/159644.
English Abstract for JP2000/11626.
English Abstract of JP2000258382.
EP 1 119 637 Opposition (1) Opposition Brief of Agamatrix, Dec. 22, 2004.
EP 1 119 637 Opposition (3) Response by Abbott, Oct. 1, 2005.
EP 1 119 637 Opposition (5) First Supplemental Brief of Agamatrix, Jun. 22, 2006.
EP 1 269 173 Opposition (3) Opposition of Proprietor's Submission Under Rule 116 EPC, Sep. 10, 2008.
EP 1 269 173 Opposition (4) Opposition Observations of Roche Diagnostics GmbH's, Sep. 11, 2008.
Feldman et al, FreeStyle TM: A Small-Volume Electrochemical Glucose Sensor for Home Blood Glucose Tsting, Diabetes Technology & Therapeutics, 2000, vol./Issue No. vol. 2, No. 2, Mary Ann Liebert, Inc.
First Supplemental Opposition Brief Against European Patent 1 119 637 by Roche Diagnostics GmbH, Jun. 9, 2006.
Gregg, Brian A. and Heller, Adam, "Cross-Linked Redox Gels Containing Glucose Oxidase for Amperometric Biosensor Applications", Anal. Chem. 1990, 62, 258-263.
Gullbault et al., "An Enzyme Electrode for the Amperometric Determination of Glucose," Analytica Chimica Acta, 64.
Hintsche, R. et al., "Chip Biosensors on Thin-Film Metal Electrodes", Sensors and Actuators, B, 4, 1991, pp. 287-291.
Internal (Non-Public) Roche Report entitled "ALCM Meeting—Aug. 21-23, 2000" (TX-361).
Internal (Non-Public) Roche Report entitled "Consumer Meter Comparison Chart" dated Nov. 30, 2006.
Internal (Non-Public) Roche Report titled "Electrochemical Systems DR-S" dated Jun. 10, 2000.
Internal (Non-Public) Roche Report titled "Electrochemical Systems DR-S" dated Oct. 6, 2000.
Jin et al., "Application of the Finite Analytic Numerical Method. Part 1. Diffusion Problems on Coplanar and Elevated Interdigitated Microarray Band Electrodes," J. Electroanal. Chem. 441 (1996), pp. 29-36.

(56) References Cited

OTHER PUBLICATIONS

JPO machine-generated translation of Aoyama JP 11-064271 A, downloaded Feb. 7, 2014, patent published Mar. 5, 1999.
Lee, Jae-Suk; Nakahama, Seiichi; and Hirao, Akira, "A New Glucose Sensor Using Microporous Enzyme Membrane", Sensors and Actuators B, 3 (1991) 215-219.
Lei et al., Studies on employing tetrathiafulvalene as an electron shuttle incorporated in a montmotillorite-modified immobilization matrix for an enzyme electrode, Journal of Electroanalytical Chemistry, pp. 93-98, issue/vol. 419.
Letter regarding European Patent Application No. 98906328.4-2204 TheraSense, Inc., Mar. 23, 2001.
Lifescan Owner's Booklet Entitled "The Comfort of Control" printed in 2003 from http://www.lifescan.com/pdf/ultra_ob.pdf.
Lifescan pamphlet entitled "Blood Glucose Monitoring Systems—Current Technologies" downloaded from www.lifescan.com/pdf/hospital/eb_110a.pdf, Lifescan 1998.
Lifescan press release for the One Touch Ultra System (downloaded Oct. 9, 2004 from www.lifescan.com/company/about/press/prulta.
Lifescan Product Brochure for OneTouch Ultra Blood Glucose Monitoring System.
Lifescan product brochure for OneTouch® Ultra™ Test Strip.
Losada et al., "Glucose-Amperometric Sensor Based on Covalent Immobilization Glucose Oxidase in Poly-2-aminoanaline Film via Chloranil on Platinized Platinum Electrode", Electroanalysis, 1997 vol./Issue No. 9, 18.
Malitesta, Cosimino; Palmissano, Francesco; Torsi, Luisa; and Zambonin Pier Giorgio, "Glucose Fast-Response Amperometric Sensor Based on Glucose Oxidase Immobilized in an Electropolymerized Poly(o-phenylenediamine) Film", Anal. Chem. 1990, 62, 2735-2740.
McMahon et al., "Detection Technologies—Taking a fresh look at sensors", downloaded from www.devicelink.com/ivd/archive/02.html originally published in IVD Technology Apr. 2002.
MediSense Optium Test Strip Package insert dated Apr. 28, 2005.
Miao, Y.; Chia, L.S.; Goh, N.K.; and Tan, S.N., "Amperometric Glucose Biosensor Based on Immobilization of Glucose Oxidase in Chitosan Matrix Cross-Linked with Glutaraldehyde", Electroanalysis 2001, 13, No. 4.
Mizutani et al. CAPLUS abstract of Amperomatric glucose sensor using a polyion complex-enzyme bilayer system, Chemica Sensors 1997, 13 Suppl B. proceedings of the 25th Chemical Sensor Symposium 1997, pp. 37-40.
Mizutani et al. CAPLUS abstract of Amperomatric enzyme electrode wit fast response to glucose using a layer of lipid-modified glucose oxidase and Nflon anionic polymer, Analytic Chimica Acta 1993, 274(2), 201-7.
Mizutani et al., Rapid measurement of transaminase activites using an amperometric L-glutamate-sensing electrode based on a glumate oxidase-poluion complex-bilayer membrane, Sensors and Actuators B 52 (1998 23-29.
Morales et al., Hydrogen peroxide amperometric biosensor base ona peroxidase-graphite-epoxy biocomposite, Analytica Chimica Acta 332 1996 131-138.
Morris et al., "An Electrochemical Capillary Fill Device for the Analysis of Glucose Incorporating Glucose Oxidase and Ruthenium (III) Hexamine as Mediator," Electroanalysis, 1992, pp. 1-9, vol. 4.
Nishihara et al., "Interdigitated Array Electrode Diffusion Measurementsin Donor/Acceptor Solutions in Polyether Electrolyte Solvents," Anal. Chem. 1991, 64, pp. 2955-2960.
Niwa, O.; Morita, M.; and Tabai H., "Electrochemical Behavior of Reversible Redox Species at Interdigitated Array Electrodes With Different Geomeetries: Consideration of Redox Cycling and Collection Efficiency" Anal. Chem. 62 (1990) 447-452.
Niwa, Osamu et al.; Fabrication and Characteristics of Vertically Separated Interdigitated Array Electrodes; J. Electroanal. Chem.; 1989; 291-297; 267; The Netherlands.
One Touch Ultra (04)—"Quick Start Guide", 2003.
Opposition Brief Against European Patent 1 119 637 by Roche Diagnostics GmbH, Dec. 23, 2004.
Opposition Brief Against European Patent 1 269 173 by Roche Diagnostics GmbH, May 16, 2006.
Owner's Booklet entitled "The Comfort of Control" by Lifescan.
Package Insert for OneTouch Ultra Test Strips for Testing Glucose in Whole Blood, Lifescan 2000.
Paeschke et al., "Properties of Interdigital Electrode Arrays with Different Geometries." Analytical Chimica Acta 305 (1995), pp. 126-136.
Petition to Make Special, Statement in Support and Exhibit F, filed Mar. 5, 2003 (TX-693).
Photocopies of the front and back portions of the commercial product marketed by Lifescan as the OneTouch made public at least as early as 2001.
Photocopies of the front and back portions of the packaging for the commercial product marketed by Lifescan as the OneTouch Ultra System.
Product description of Arcare 7840 obtained from www.adhesiveresearch.com on Jun. 16, 2006.
Response to Opposition of EP 1269173 dated May 3, 2007—Diabetes Diagnostics, Inc.
Rishon et al, CAPLUS abstract of Amperometric glucose sensors based on glucose oxidase immobilized in Naflon, Electroanalysis 1994, 6(1) 17-21.
*Roche Diagnostics Operations, Inc. et al.* v. *Lifescan Inc. and Nova Biomedical Corp.*, Appeal from US District Court District of Delaware 07-CV-0753, decision dated Jan. 25, 2012.
*Roche Diagnostics Operations, Inc. et al.* v. *Abbott Diabetes, Care, Incorporated et al.*, "Complaint for Patent Infringement" filed Nov. 21, 2007, US District Court for the Distriction of Delaware, Civil Action No. 07-753.
*Roche* v. *Abbott* Memorandum Opinion dated Dec. 5, 2014.
*Roche* v. *Abbott et al.* 02—Abbott's Answer, Jan. 11, 2008.
*Roche* v. *Abbott et al.* 04—LifeScan's Answer, Jan. 11, 2008.
*Roche* v. *Abbott et al.* 06—Nova's Answer Exhibits A and B, Jan. 11, 2008.
*Roche* v. *Abbott et al.* 07—Nova's Amended Answer, Feb. 8, 2008.
*Roche* v. *Abbott et al.* 08—Nova's Amended Answer Exhibits 1 and 2, Feb. 8, 2008.
*Roche* v. *Abbott et al.* 09—Roche's Amended Complaint, Jan. 11, 2008.
*Roche* v. *Abbott et al.* 15—LifeScan's Second Supplemental Interrogatory Responses, Nov. 25, 2008.
*Roche* v. *Abbott et al.* 23—Roche's Reply (Exhibit A to Motion to File), Oct. 21, 2009.
*Roche* v. *Abbott* Remand 01—Roche's Opening Brief on Claim Construction, Jun. 8, 2012.
*Roche* v. *Abbott* Remand 02—Defendants' Opening Brief on Claim Constructions, Aug. 1, 2012.
*Roche* v. *Abbott* Remand 03—Roche's Reply Brief on Claim Construction, Aug. 15, 2012.
Sandy LaMere email to Nigel Surridge dated Sep. 11, 2002 (TX-625).
Second Supplemental Oppositon Brief Against European Patent 1 119 637 by Roche Diagnostics GmbH, Oct. 13, 2006.
TheraSense Press Release titled "About Us", dated Aug. 1, 2000 (TX-345).
Translation of JP H05[1993]-312761.
Translation of JP H10[1998]-02874.
Translation of JP H11[1999]-108879.
Translation of JP H11[1999]-125618.
Translation of JP H11[1999]-94790.
Translation of JP H11[1999]-94791.
Ullah et al., "Can Temporal Analysis of Optical Coherenece Tomography Statistics Report on Dextrorotary-Glucose Levels in Blood?", Laser Physics, 2011, vol. 21, No. 11, pp. 1962-1971.
Urban et al., "Chemo- and Biosensor Microsystems for Clinical Applications," Part of the SPIE Conference on Chemical Microsensors and Applications, Boston, MA Nov. 1998 SPIE vol. 3539.
US District Court of Delaware Civil Action No. 07-753-JJF, Answer and Affirmative Defense to Amended Complaint for Patent Infrigement by Defendant Bayer Healthcare, LLC, filed May 5, 2008.

(56) References Cited

OTHER PUBLICATIONS

US District Court of Delaware Civil Action No. 07-753-JJF, Answer and Counterclaims of Defendant LifeScan, Inc. to Plaintiffs' Amended Complaint for Patent Infringement, filed Apr. 29, 2008.
US District Court of Delaware Civil Action No. 07-753-JJF, Answer, Affirmative Defenses, and Counterclaims of Defendant Nova to Plaintiffs' Amended Complaint for Patent Infringement, filed May 5, 2008.
US District Court of Delaware Civil Action No. 07-753-JJF, Opening Brief in Support of Defendants Abbott Diabetes Care Inc.'s and Abbott Diabetes Care Sales Corp's Rule 12(B)(6) Motion to Dismiss Infringement Claims, filed May 5, 2008.
US District Court Northern District of California Case No. C 04-2123, C 04-3327, C 04-3732—Abbott's Reply Markman Brief, Dec. 20, 2006.
US District Court Northern District of California Case No. C 04-2123, C 04-3327, C 04-3732—Becton Dickinson's Opening Markman Brief, Dec. 1, 2006.
US District Court Northern District of California Case No. C 04-2123, C 04-3327, C 04-3732—Becton Dickson's Reply Markman Brief, Dec. 20, 2006.
US District Court Northern District of California Case No. C 05-3177—Abbott's Opening Markman Brief, Dec. 1, 2006.
US District Court Northern District of California Case No. C 05-3177—Abbott's Reply Markman Brief, Dec. 20, 2006.
US District Court Northern District of California Case No. C 05-3177—Abbott's Reply to Counterclaims, Nov. 8, 2005.
US District Court Northern District of California Case No. C 05-3177—Bayer's Reply Markman Brief, Dec. 20, 2006.
US District Court Northern District of California Case No. C 05-3177—Roche and Bayer's Opening Markman Brief, Dec. 1, 2006.
US District Court Northern District of California Case No. C 05-3177—Roche's Answer to First Amended Complaint, Oct. 18, 2005.
US District Court Northern District of California Case No. C 05-3177—Roche's Answer, Aug. 22, 2005.
US District Court Northern District of California Case No. C 05-3177—Roche's Preliminary Invalidity Contentions, Dec. 9, 2005.
US District Court Northern District of California Case No. C 05-3177—Roche's Reply Markman Brief, Dec. 20, 2006.
US District Court Northern District of California Case No. C 05-3177—Roche's Second Amended Preliminary Invalidity Contentions, Sep. 15, 2006.
US District Court Northern District of California Case No. C 04-2123, C 04-3327, C 04-3732—Abbott's Opening Markman Brief, Dec. 1, 2008.
US District Court Northern District of California Case No. C 05-3177—Docket Report, Mar. 22, 2007.
US District Court, District of Delaware Civil Action No. 07-753-JJF, Defendants' Opening Claim Construction Brief dated Nov. 24, 2008.
US District Court, District of Delaware Civil Action No. 07-753-JJF, Nova's Supplemental Responses to Roche's Interrogatories (Nos. 1-5, 7-9, 12, 18-24, and 26-27), dated Nov. 26, 2008.
US District Court, District of Delaware Civil Action No. 07-753-JJF, Roche's Opening Markman Brief dated Nov. 24, 2008.
WO 2001/041643 International Application Status Report, English Translation.
Wollenberger et al., "Interdigitated Array Microelectrodes for the Determination of Enzyme Activities," Analyst, Jun. 1994, pp. 1245-1249.
Xin et al, Enzyme modified amperometric sensors for choline and acetylene with tetrathiafulvalene tetracyanoquinodimethane as the electron-transfer mediator, Analytica Chimca Acta 341 (1997) 43-51).
"A New Glucose Sensor Using Microporous Enzyme Membrane", Lee et al, Sensors and Actuators, pp. 215-219, issue/vol. B, 3.
"Hematocrit" entr in the online Family Practice Notebook [online] [retrieved on Jun. 22, 2016]. Retrieved from the internet <URL: http://www.fpnotebook.com/hemeonc/lab/Hmtcrl.htm.
Lee et al, "A New Glucose Sensor Using Microporous Enzyme Membrane", Sensors and Actuators, pp. 215-219, issue/vol. B,3.
US Court of Appeals for the Federal Circuit decision dated Sep. 22, 2016, *Roche Diagnostics Operations, Inc., Corange International Limited*, v. *Lifescan Incorporated, Nova Biomedical Corporation*, Case 15-1356, Appeal from the US District Court for the District of Delaware in No. 1:07-cv-00753-RGA, 13 pages.

* cited by examiner

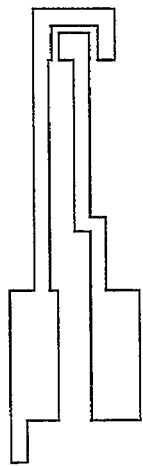 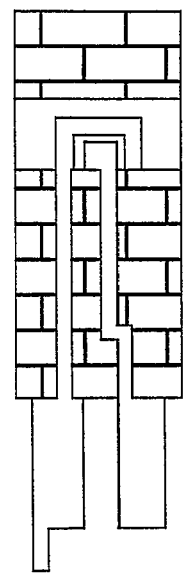
*Fig. 9*  *Fig. 9A*

DETERMINING BLOOD GLUCOSE IN A SMALL VOLUME SAMPLE RECEIVING CAVITY AND IN A SHORT TIME PERIOD

REFERENCE TO RELATED APPLICATIONS

This application is a continuation of U.S. patent application Ser. No. 14/695,528, filed Apr. 24, 2015, now U.S. Pat. No. 9,638,658, which is a continuation of U.S. patent application Ser. No. 13/929,293, filed Jun. 27, 2013, now U.S. Pat. No. 9,017,544, which is a continuation of U.S. patent application Ser. No. 13/719,967 filed Dec. 19, 2012, now abandoned, which is a continuation of U.S. patent application Ser. No. 13/433,779, filed Mar. 29, 2012, now U.S. Pat. No. 8,349,168, which is a continuation of U.S. patent application Ser. No. 13/339,598, filed Dec. 29, 2011, now U.S. Pat. No. 8,303,801, which is a continuation of U.S. patent application Ser. No. 12/477,239, filed Jun. 3, 2009, which is a continuation of U.S. patent application Ser. No. 11/677,737 filed Feb. 22, 2007, which is a continuation of U.S. patent application Ser. No. 10/382,322, filed Mar. 5, 2003, now U.S. Pat. No. 7,276,147, which is a continuation-in-part of U.S. patent application Ser. No. 10/264,785 filed Oct. 4, 2002, now abandoned, which are hereby incorporated by reference in their entirety. U.S. patent application Ser. No. 11/677,737 is also a continuation-in-part of U.S. patent application Ser. No. 10/264,891, filed Oct. 4, 2002, now U.S. Pat. No. 7,276,146, which is hereby incorporated by reference in its entirety.

FIELD OF THE INVENTION

The present invention relates to methods for determining the concentration of glucose in a blood sample, and particularly to methods using test strips having a sample receiving cavity having a volume from about 0.3 µl to less than 1 µl and determining the concentration of glucose within a time period from about 3.5 seconds to about 8 seconds after detecting the blood sample in the sample receiving cavity.

BACKGROUND

Electrodes are well known devices which permeate industry, and which, although often very small in size and not particularly visible, can have a significant impact on peoples' lives. Electrodes are used in electronic instruments having many industrial, medical, and analytical applications. To name just a few, they include monitoring and controlling fluid flow, and various types of analytical methods wherein electric current is measured to indicate the presence or concentration of certain chemical species.

With respect to analytical methods, the need for detection and quantitative analysis of certain chemicals found within a larger composition can be important for the chemical and manufacturing industries, as well as biotechnology, environmental protection, and health care industries. Examples of substances that may be analyzed include liquid samples such as tap water, environmental water, and bodily fluids such as blood, plasma, urine, saliva, interstitial fluid, etc.

Many analytical techniques, sometimes referred to as electrochemical detection methods, make use of electrodes as a component of an electrochemical sensor. The sensors are used in combination with electronic apparatuses to precisely detect the presence or concentration of a selected chemical species (analyte) within a substance sample. Techniques that allow the use of miniaturized disposable electroanalytic sample cells for precise micro-aliquot sampling, and self-contained, automatic means for measuring the analyte, can be particularly useful.

Electrochemical detection methods can include amperometric measurement techniques, which generally involve measurement of a current flowing between electrodes that directly or indirectly contact a sample of a material containing an analyte, and studying the properties of the current. The magnitude of the current can be compared to the current produced by the system with known samples of known composition, e.g., a known concentration of analyte, and the quantity of analyte within the sample substance can be deduced. These types of electrochemical detection methods are commonly used because of their relatively high sensitivity and simplicity.

Micro-electrode arrays are structures generally having two electrodes of very small dimensions, typically with each electrode having a common element and electrode elements or micro-electrodes. If "interdigitated" the arrays are arranged in an alternating, finger-like fashion (See, e.g., U.S. Pat. No. 5,670,031). These are a sub-class of micro-electrodes in general. Interdigitated arrays of micro-electrodes, or IDAs, can exhibit desired performance characteristics; for example, due to their small dimensions, IDAs can exhibit excellent signal to noise ratios.

Interdigitated arrays have been disposed on non-flexible substrates such as silicon or glass substrates, using integrated circuit photolithography methods. IDAs have been used on non-flexible substrates because IDAs have been considered to offer superior performance properties when used at very small dimensions, e.g., with feature dimensions in the 1-3 micrometer range. At such small dimensions, the surface structure of a substrate (e.g., the flatness or roughness) becomes significant in the performance of the IDA. Because non-flexible substrates, especially silicon, can be processed to an exceptionally smooth, flat, surface, these have been used with IDAs.

SUMMARY OF THE INVENTION

Whereas micro-electrodes have in the past been used with non-flexible substrates such as silicon, ceramic, glass, aluminum oxide, polyimide, etc., it has now been discovered that micro-electrode arrays, for example, IDAs, can be advantageously useful when disposed on flexible substrates. Moreover, such micro-electrodes, disposed on flexible surfaces, can be prepared using methods that involve flexible circuit photolithography, as opposed to methods relating to integrated circuit photolithography.

An interdigitated array of the invention, disposed on a flexible substrate, can be used generally, in applications where IDAs are known to be usefully employed. In particular embodiments of the invention, the IDAs can be used to construct electrochemical sensors, test cells, or test strips. The sensors can be used with electronic detection systems (sometimes referred to as "test stands") in methods of analyzing sample compositions for analytes. Preferred embodiments of sensors can be disposable, and can include channels or microchannels, preferably a capillary, which facilitates flow of a substance sample into the reaction chamber and in contact with the sensor.

The micro-electrode arrays of the invention can be useful when disposed onto a flexible substrate. In particular, IDAs are shown to be effective at dimensions relatively larger than the dimensions often used for IDAs disposed on non-flexible substrates. Even though they can be relatively larger than IDAs disposed on non-flexible substrates, the inventive IDAs are still able to exhibit performance properties, e.g., signal to noise amplification benefits and steady-state assay profiles, comparable to IDAs having smaller dimensions.

Electrochemical sensors of the invention have been found to provide performance advantages, e.g., relative to commercially available sensors. For sensors used in glucose monitoring, compared to commercially available sensors, the inventive sensors can exhibit improved (shortened) processing periods, e.g., one half second to steady-state after application of the assay potential and 5 seconds to readout, and the ability to get an accurate and precise readout from a relatively small sample of substance, e.g., less than one microliter (μl), preferably a sample volume in the range from about 0.25 to 1.0 μl, e.g., from about 0.4 to about 1.0 μl.

The use of larger-dimensioned micro-electrode arrays also allows the significant advantage of fabricating arrays and sensors using relatively less expensive and more efficient flex circuit photolithography processes. These can advantageously incorporate the use of solid materials instead of spin-on liquid materials, e.g., one or more of a solid photoresist or a solid coverlay, instead of liquid materials typically used in integrated circuit photolithography.

An aspect of the invention relates to micro-electrodes used in combination with a flexible substrate. The array can include a working electrode and a counter electrode, each including a common lead and commonly-connected electrode elements, for example with the electrode elements being arranged in a substantially-parallel, alternating fashion. Preferred dimensions for micro-electrodes can be, e.g., feature size or width of electrodes ($W_e$) in the range from 15 or 20 or 25 μm, up to about 100 μm, more preferably from greater than or about 25 or 30 μm to about 50 μm. Preferred spacing between electrodes ($W_g$) can also be in the range from about 15 to about 50 μm, more preferably from greater than or about 20 or 25 μm to about 45 μm.

Another aspect of the invention relates to an electrochemical sensor comprising an array of micro-electrodes disposed on a flexible substrate. The sensor can further include a chemical coating disposed on the array to facilitate practice of electrochemical detection methods.

Yet another aspect of the invention relates to a method of detecting an analyte using an array of micro-electrodes of the invention, e.g., using an electrochemical sensor comprising an interdigitated array disposed proximal to a flexible substrate. Such a method can include certain of the following steps. A sensor is provided which comprises micro-electrodes proximal to a flexible substrate, and a chemical coating proximal to the micro-electrodes; the coating comprises a compound reactive to produce an electroactive reaction product. The coating is contacted with a substance comprising an analyte, allowing the analyte to react with chemical components of the coating to produce an electroactive reaction product. Electric properties of the coating can be measured, and the electric properties can be correlated to the amount of electroactive reaction product, and to the amount of analyte.

Still another aspect of the invention relates to a method of preparing a micro-electrode, including the step of disposing the micro-electrode onto a flexible substrate.

More particularly, the present invention comprises a method for determining the concentration of glucose in a blood sample. The method utilizes a disposable test strip having a sample receiving cavity having a volume from about 0.3 μl to less than 1 μl, and including a reagent containing an enzyme and a mediator. The reagent reacts with glucose to produce an electroactive reaction product. The method involves providing a blood sample to the sample receiving cavity, detecting the presence of the blood sample in the sample receiving cavity, and thereafter determining the glucose concentration within a time period from about 3.5 seconds to about 8 seconds after detecting the presence of the blood sample.

BRIEF DESCRIPTION OF THE DRAWINGS

FIG. 9 shows a top plan view of an alternative embodiment of a pair of electrodes in accordance with the invention.

FIG. 9A shows a top plan view of an alternative embodiment of a sensor incorporating the electrode pair of FIG. 9.

DETAILED DESCRIPTION

Figure 1:
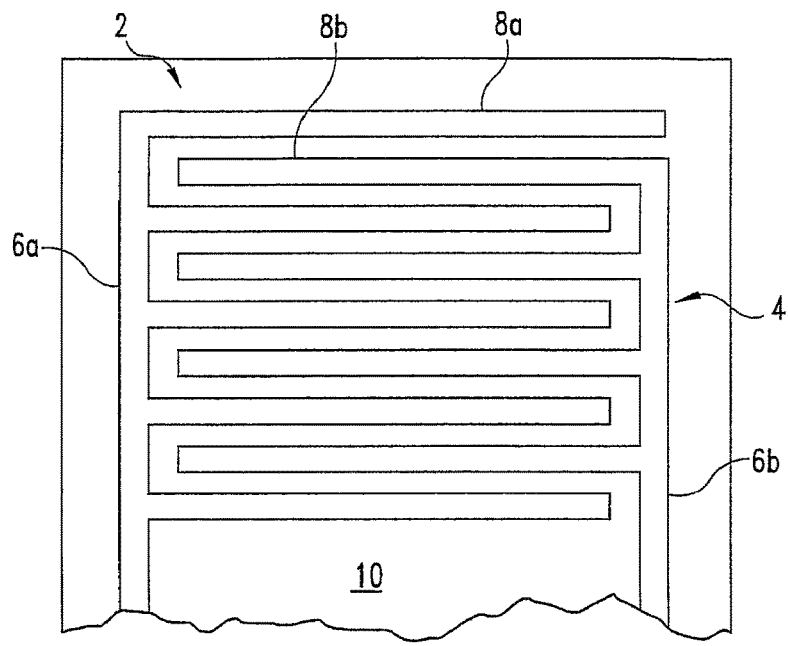
FIG. 1 shows an embodiment of an interdigitated array of electrodes in accordance with the invention.

An embodiment of the present invention is directed to arrays of micro-electrodes, e.g., an interdigitated array of electrodes (sometimes referred to as "microband" electrodes) used in combination with a flexible substrate.

An array of micro-electrodes includes two electrodes, referred to as the working electrode and the counter electrode, electrically insulated from one another.

Micro-electrodes, as distinguished from other electrodes generally, are understood in the electronic and biosensor arts. In analyzing a liquid sample using electrodes and electronic equipment and techniques, the size and spacing of electrodes can affect whether diffusion of an analyte through the sample to an electrode occurs by a planar or non-planar path. Micro-electrode arrays are of a size and spacing such that in detecting chemical species of a solution, the species will diffuse toward or approach an electrode of the micro-electrode array in a non-planar fashion, e.g., in a curved or hemispherical path of diffusion. In contrast, non-microelectrodes, i.e., "macro-electrodes," cause diffusion of an analyte through a solute according to a substantially planar path. It is also understood that some electrode configurations can cause diffusion to take place by a mix of planar and non-planar paths, in which case the electrodes can be considered a micro-electrode array, especially if the diffusion occurs predominantly (e.g., greater than 50%) according to a non-planar path, or if the size of the electrodes is less than 100 μm, e.g., less than 50 μm.

The electrodes of a micro-electrode array are positioned near each other in an arrangement that will result in non-planar diffusion as described. The arrangement of the electrodes can be any arrangement that results in such diffusion, with a working and a counter electrode being substantially evenly spaced from each other. One electrode may be arranged into a shape or figure or outline that will produce interstices within which the second electrode may be placed. For instance, one electrode can be arranged as an increasing radius, substantially circular spiral, with a continuous, long and narrow interstitial area being created between each successively larger revolution of electrode. The other electrode can be positioned in the interstitial area between revolutions, while the electrodes remain insulated from one another. The width and spacing of the electrodes can be arranged to result in micro-electrode array performance.

According to other forms of such micro-electrode arrays, the spiral may not be substantially circular, but could include linear, square, angled, or oblong or oval features. Or, the electrodes could be arranged in any other geometric form whereby the electrodes are placed adjacent to each other and within the other's respective interstitial area, e.g., by following a similar path separated by a substantially uniform gap.

In one particular embodiment, the micro-electrode can be arranged into an interdigitated array, meaning that at least a portion of electrode elements of the working electrode are placed substantially parallel to and in alternating succession with at least a portion of the electrode elements of the counter electrode, e.g., in an alternating, "finger-like" pattern. Such interdigitated micro-electrode arrays include electrode elements (sometimes referred to as "fingers") and a common element ("contact strip") which commonly connects the electrode elements.

The components of the electrodes may be made of any conductive material, including those known and conventionally used as electrode materials, particularly including materials known in the flexible circuit and photolithography arts. These can include, for example, carbon, noble metals such as: gold, platinum, palladium, alloys of these metals, potential-forming (conductive) metal oxides and metal salts, as well as others.

The electrodes and their components can be of dimensions, meaning the width of the electrode components as well as the separation between components, that can provide an array with useful properties, e.g., useful or advantageous capabilities with respect to contacting a substance or measuring electrical properties. Advantageously, interdigitated arrays can be prepared at dimensions that allow for contact with and measurement of electrical properties of a relatively small sample of a substance.

In preferred embodiments of the invention, each electrode element can independently have a width ($W_e$) in the range from greater than 15 micrometers ($\mu m$) to about 50 $\mu m$, with the range from greater than or about 20 or 25 $\mu m$ to about 40 $\mu m$ being particularly preferred. The separation between electrode components ($W_g$), especially the separation between alternating electrode elements, can also preferably be in the range between about 15 micrometers and about 50 $\mu m$, with the range from greater than or about 20 or 25 $\mu m$ to about 40 $\mu m$ being particularly preferred. The total area of an electrode (meaning the area of the fingers but not the common element) can be chosen depending on these dimensions, on the use intended for the electrode, on the desired current level intended to pass through the electrode, and on the desired number of electrode elements. An exemplary area of an electrode having 10 electrode elements can be in the range from about 0.1 to about 0.5 square millimeters, (for example 10 electrode fingers having dimensions of 50 $\mu m$ by 1 mm), e.g., from about 0.2 to 0.3.

The thickness of the electrode components can be sufficient to support a desired electric current. Exemplary thicknesses can be in the range from about 30 to 200 nanometers (nm), with a preferred thickness being about 100 nm.

The electrodes can independently have a number of interdigitated electrode elements sufficient to provide utility, e.g., allowing contact with a substance to measure its electrical behavior. Conventionally, the array can have substantially the same number (equal, plus or minus one) of electrode elements in the working electrode as are in the counter electrode, allowing the electrode elements to be paired next to each other in an alternating sequence. In some preferred embodiments of the array, such as in some of the applications described below for electrochemical sensors, each electrode of an array may typically have from about 4 to about 30 electrode elements.

FIG. 1 illustrates an embodiment of an array of the invention. Working electrode 2 and counter electrode 4 are arranged as an interdigitated array on flexible substrate 10. (The figure is not to scale and its dimensions, as well as the dimensions of the other figures, should not be construed to limit the invention). The working and counter electrodes include common strips 6a and 6b, respectively, which can be connected to electrically conductive means (e.g., "connectors," "pads," or "leads," etc.) for connecting the electrodes to an external circuit. In the illustrated example, the working electrode includes electrode elements 8a connected to common strip 6a, and the counter electrode includes electrode elements 8b connected to common strip 6b.

According to the invention, the interdigitated array is disposed proximal to, e.g., on, a flexible substrate. To act as a flexible substrate, a material must be flexible and also insulating, and is typically relatively thin. The substrate should be capable of adhering components of an IDA, or additional components of a sensor, to its surface. Such thin, insulative, flexible substrates are known in the art of flexible circuits and flex circuit photolithography. "Flexible substrates" according to the present disclosure can be contrasted to non-flexible substrates used in integrated circuit (IC) photolithography but not in flexible circuit photolithography. Examples of non-flexible substrates used in IC photolithography include silicon, aluminum oxide, and other ceramics. These non-flexible substrates are chosen to be processable to a very flat surface. Typical flexible substrates for use in the invention are constructed of thin plastic materials, e.g., polyester, especially high temperature polyester materials; polyethylene naphthalate (PEN); and polyimide, or mixtures of two or more of these. Polyimides are available commercially, for example under the trade name Kapton®, from I.E. duPont de Nemours and Company of Wilmington, Del. (duPont). Polyethylene naphthalate is commercially available as Kaladex®, also from duPont. A particularly preferred flexible substrate is 7 mil thick Kaladex® film.

Interdigitated arrays of the invention can be used in applications generally known to incorporate electrodes, especially applications known to involve interdigitated arrays of electrodes. Various applications are known in the arts of electronics and electrochemistry, including applications relating to process and flow monitoring or control, and chemical analytical methods. The arrays may be particularly useful as a component of an electrochemical sensor, where there is added value, benefit, or cost efficiency, to the use of a flexible substrate, or where there is value, benefit, or cost efficiency in having an interdigitated array of dimensions relatively larger than the dimensions of interdigitated arrays conventionally disposed on non-flexible substrates.

An interdigitated array of the invention can, for example, be included in an electrochemical sensor (sometimes referred to as a "biosensor" or simply "sensor") used in electrochemical detection methods. Electrochemical detection methods operate on principles of electricity and chemistry, or electrochemistry, e.g., on principles of relating the magnitude of a current flowing through a substance, the resistance of a substance, or a voltage across the substance given a known current, to the presence of a chemical species within the substance. Some of these methods can be referred to as potentiometric, chronoamperometric, or impedance, depending on how they are practiced, e.g., whether potential difference or electric current is controlled or measured. The methods and sensors, including sensors of the invention, can measure current flowing through a substance due directly or indirectly to the presence of a particular chemical compound (e.g., an analyte or an electroactive compound), such as a compound within blood, serum, interstitial fluid, or another bodily fluid, e.g., to identify levels of glucose, blood urea, nitrogen, cholesterol, lactate, and the like. Adaptations of some electrochemical methods and electrochemical sensors, and features of their construction, electronics, and electrochemical operations, are described, for example, in U.S. Pat. Nos. 5,698,083, 5,670,031, 5,128,015, and 4,999,582, each of which is incorporated herein by reference.

Oftentimes, a compound of interest (analyte) in a substance is not detected directly but indirectly, by first reacting the analyte with another chemical or set of chemicals proximal to or in contact with an IDA. The reaction produces an electroactive reaction product that is electrochemically detectable and quantifiable by applying a potential difference between the counter and working electrodes and measuring the magnitude of the current produced. This allows measurement of the amount of electroactive reaction product generated by the first reaction, and correlation of that measurement to the amount of analyte in the sample substance.

An example of such a method involves the catalytic use of an enzyme, and is sometimes referred to as enzymatic amperometry. These methods can use an interdigitated array of electrodes coated with a chemical coating that contains a chemical compound reactive to produce an electroactive reaction product. (The chemical compound reactive to produce an electroactive reaction product is sometimes referred to herein as a "mediator.") Upon contacting the coating with a sample that contains an analyte, analyte reacts with chemical compounds of the coating to generate electroactive reaction product. This electroactive reaction product can be electronically detected, measured, or quantified, by applying a potential difference between the electrodes and measuring the current generated by the electrooxidation of the mediator at the working electrode. By calibrating the system's behavior using known substances and concentrations, the electrical behavior of the system in the presence of a sample substance of unknown composition can be determined by comparison to the calibration data.

The sensor of the invention may be used in amperometric applications, e.g., enzymatic amperometric applications, if disposed on the array is a coating of useful chemistry, including e.g., an enzyme and a mediator. When a sample containing an analyte is contracted with the coating, the analyte, enzyme, and the mediator participate in a reaction, wherein the mediator is either reduced (receives at least one electron) or is oxidized (donates at least one electron). Usually, in this reaction, the analyte is oxidized and the mediator is reduced. After this reaction is complete, an electrical potential difference can be applied between the electrodes. The amount of reducible species and the applied potential difference must be sufficient to cause diffusion-limited electrooxidation of the reduced form of the mediator at the surface of the working electrode. The IDA electrode configuration of the sensor places the working electrode fingers in close proximity to counter electrode fingers. Mediator electrooxidized at the working electrode can therefore diffuse rapidly to the adjacent counter electrode via radial diffusion where it is once again reduced. Likewise, oxidized mediator reduced at the counter electrode can migrate to the working electrode for electrooxidation to the oxidized form. This migration between the fingers produces a constant or "steady state" current between the electrodes. After a short time delay, this steady state current is measured and correlated to the amount of analyte in the sample.

The chemistries of the first and second reactions can be of any nature effective to produce the electroactive reaction product of the first reaction, to detect or quantify the electroactive reaction product during the second reaction, and to allow correlation of the amount of electroactive reaction product with the presence or concentration of analyte in the original sample.

In general, a typical first reaction can be an oxidation/reduction sequence, preferably occurring without the need for a chemical potential across the electrodes. It can be desirable for this reaction to favor maximum, preferably complete conversion of the analyte, and to proceed as quickly as possible. Often this reaction is catalyzed, e.g., enzymatically. Such reaction schemes and their application to enzymatic amperometry are known. See, e.g., U.S. Pat. No. 5,128,015; European Patent Specification EP 0 406 304 B1; and Aoki, Koichi, *Quantitative Analysis of Reversible Diffusion-Controlled Currents of Redox Soluble* Species *at Interdigitated Array Electrodes Under Steady-State Conditions*, J. Electroanal. Chem. 256 (1988) 269-282. An example of a useful reaction scheme can be the reaction of a component of a bodily fluid, e.g., glucose, with an enzyme and a cofactor, in the presence of a mediator, e.g., an oxidizer, to produce an electroactive reaction product.

After the reaction is complete, a power source (e.g., battery) applies a potential difference between the electrodes. When the potential difference is applied, the amount of oxidized form of the redox mediator at the counter electrode and the potential difference must be sufficient to cause diffusion-limited electrooxidation of the reduced form of the redox mediator at the working electrode surface. In this embodiment, the close proximity of the counter and working electrode fingers in the IDA electrode configuration aids in the fast radial diffusion of the reduced and oxidized redox mediator between the electrodes. Recycling of the mediator between the electrodes and their subsequent oxidation and reduction on the electrodes generates a constant or "steady state" assay current. This steady state assay current is measured by a current measuring meter.

The measured current may be accurately correlated to the concentration of analyte in the sample when the following requirements are satisfied:

1) the rate of oxidation of the reduced form of the redox mediator is governed by the rate of diffusion of the reduced form of the redox mediator to the surface of the working electrode; and 2) the current produced is limited by the oxidation of the reduced form of the redox mediator at the surface of the working electrode.

In the preferred embodiment, these requirements are satisfied by employing a readily reversible mediator and by using a mixture of amounts of mediator and other components of the chemical layer to ensure that the current produced during diffusion limited electrooxidation is limited by the oxidation of the reduced form of the mediator at the working electrode surface. For current produced during electrooxidation to be limited by the oxidation of the reduced form of the mediator at the working electrode surface, the amount of reducible species at the surface of the counter electrode must always exceed the amount of the reduced form of the redox mediator at the surface of the working electrode.

An example of a reaction scheme relates to the detection of glucose using ferricyanide and Glucose-Dye-Oxidoreductase (Glur-Dor). The electroactive reaction product of the enzymatic reaction between glucose and the enzyme is the reduced mediator, ferrocyanide. The ferrocyanide is electrooxidized at the working electrode back to ferricyanide. One mole of oxidized redox mediator is reduced at the counter electrode for every mole of reduced redox mediator oxidized at the working electrode. Ferricyanide electrooxidized at the working electrode, diffuses to the counter electrode, and the ferrocyanide produced at the counter electrode can rapidly diffuse to the working electrode where it is again oxidized. A "quasi-steady state" concentration gradient is established between the counter and working electrode pairs resulting in generation of a constant quasi-steady state current at the working electrode.

The magnitude of the current, preferably as measured at a quasi-steady-state condition, can be correlated to the amount of electroactive reaction product present in the coating, and consequently, to the amount of analyte in the sample.

The chemical coating should allow diffusion of analyte into the coating, followed by reactions as described. The coating can include materials which can contain the reactive chemical components, which allow reaction between the components to produce an electroactive reaction product, which allow necessary diffusion of chemical components, and which can support a current passing through the coating based on the concentration of electroactive reaction product. Typically, the coating can be made up of a binder that contains a set of chemicals which react to produce an electroactive reaction product. The chemicals generally include a mediator and necessary enzymes and cofactors. Such a coating can also contain a variety of additional components to make the coating operative and suitable for processing, including specific components listed above as well as surfactants, film formers, adhesive agents, thickeners, detergents, and other ingredients and additives that will be understood by an artisan skilled in the electrochemical sensor art.

The binder can provide integrity of the coating while allowing diffusion of the different components of the reaction scheme, reaction between the reactive components, and movement of reactive components and products sufficient to produce a quasi-steady-state concentration gradient of mediator and electroactive reaction product and thereby establish a stable or quasi-steady-state current between the electrode pairs. Exemplary binders can include gelatin, carrageenan, methylcellulose, polyvinyl alcohol, polyvinylpyrrolidone, alginate, polyethylene oxide, etc. Hydroxyethylcellulose (e.g., NATROSOL 250M), sodium carboxymethylcellulose and microcrystalline cellulose (e.g., AVICEL RC-591 F), and alginic acid may also be used.

A sensor according to the invention can be understood to include a micro-electrode disposed on a flexible substrate, optionally including a chemical coating, and further including any immediate appurtenance necessary to use the sensor in an electronic system or apparatus (e.g., test stand) designed, for example, for use in an electrochemical detection method. A sensor can include the interdigitated array disposed on a flexible substrate, with additional components to independently connect each of the separate electrodes to a different voltage, e.g., electrical connectors, leads, or pads. In some circumstances, the sensor may include a reference electrode provided on the same or a different substrate and electrically insulated from the interdigitated array. The sensor may also include components to direct flow of a sample substance into contact with the IDA, e.g., a vessel, channel, microchannel, or capillary. A particularly preferred embodiment of the sensor includes a microchannel or capillary, most preferably a capillary, which directs flow of a sample substance into the reaction chamber and over the IDA (e.g., a coated IDA).

A capillary can be included in a sensor to facilitate analysis of a small volume of a sample substance by precisely directing the flow of a volume of sample over the IDA, preferably in a short period of time. Analysis of relatively small volumes of a sample substance can be accomplished, at least in part, due to the signal amplification features of the IDA.

Preferred dimensions of a capillary for what can be referred to as a "low volume sensor configuration," can be in the range of 0.025 mm to 0.2 mm (depth), preferably about 0.125 mm (depth), ×1 mm (width)×3 mm (length), resulting in a capillary chamber requiring a relatively small volume of sample, e.g., less than 400 nanoliters (nL). The volume of the chamber can preferably be such that a low volume sample of a substance can be directed into or through the chamber for analysis. Chamber volumes will vary depending on the type of analyte being studied, and even its concentration of an analyte. (Blood samples of different hematocrits will dispense differently into a capillary.) Exemplary chamber volumes can be in the range from about 100 to 300 nanoliters for glucose analysis in interstitial fluid, and from about 250 to 400 nanoliters for glucose analysis applications in the whole blood. In the most preferred embodiments of the sensor, including a capillary, the capillary may have a vent to facilitate flow of a sample substance into the capillary chamber by equalizing pressure between the interior and exterior of the chamber.

The sensor of the invention can include these and other features, and, especially if an embodiment is disposable, can be referred to as a "test strip" or a "test cell." The term "disposable" refers to sensors designed or sold for a single use, after which they are to be discarded or otherwise stored for later disposal.

Capillaries may be fabricated as a component of a sensor, using photolithographic methods, e.g., as described infra.

Figure 2:
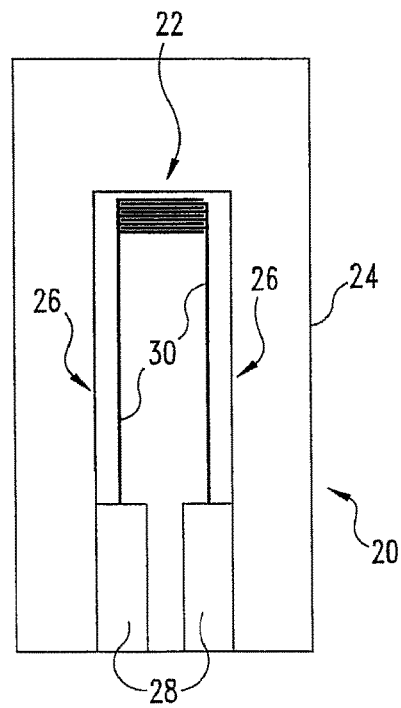
FIGS. 2 and 2A show a top view of a sensor of the invention.
Figure 2A:
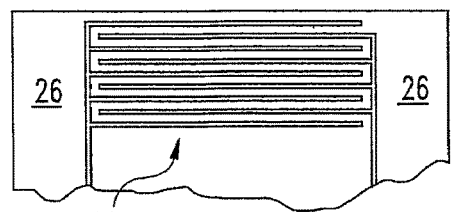

An example of a sensor construction is shown in FIG. 2, according to the preferred embodiment. The figure shows sensor 20, including an interdigitated array of electrodes 22 disposed on flexible substrate 24. The electrodes are connected to electrically-conductive connectors 26 which include portions 28 that can be identified as pads, located on the surface of the flexible substrate, where they are available to be contacted to an external electronic circuit such as a testing apparatus. The connectors also include connector portions 30, which connect electrode elements at the array to the pads, and which may typically be covered by an insulating layer. FIG. 2a shows a close-up of array 22, showing that electrodes attached to each of connectors 26 are arranged in an inter digitated fashion (as shown in FIG. 1).

Figure 3:
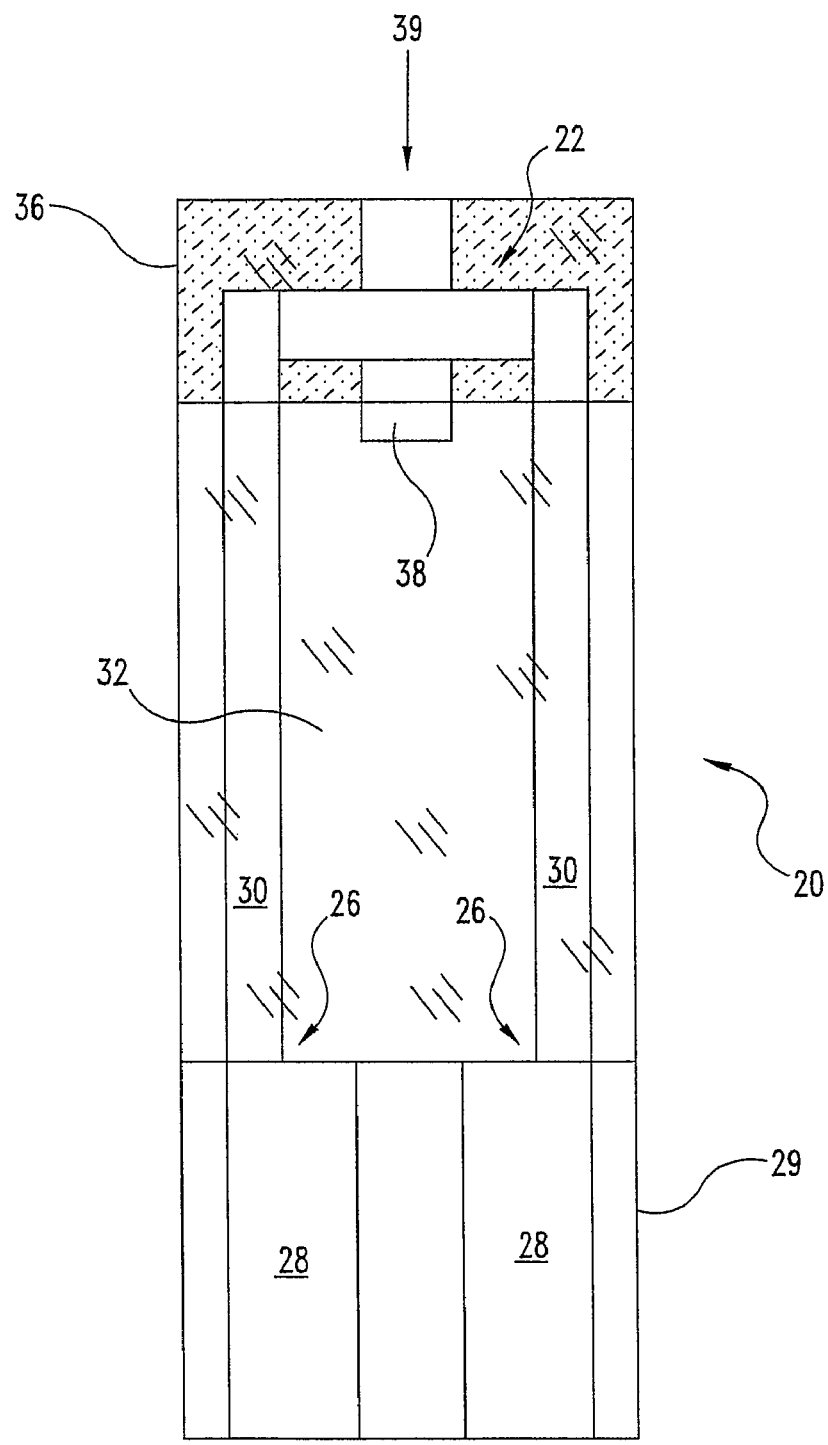
FIG. 3 shows a top view of a sensor of the invention.
Figure 4:
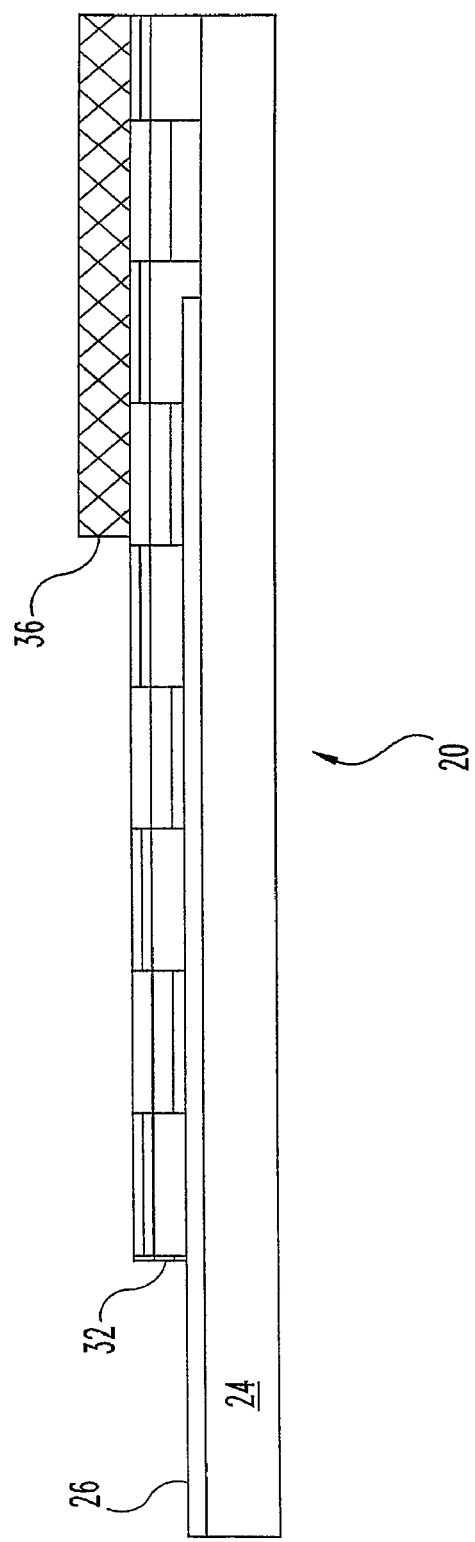
FIG. 4 shows a side view of a sensor of the invention.
Figure 5:
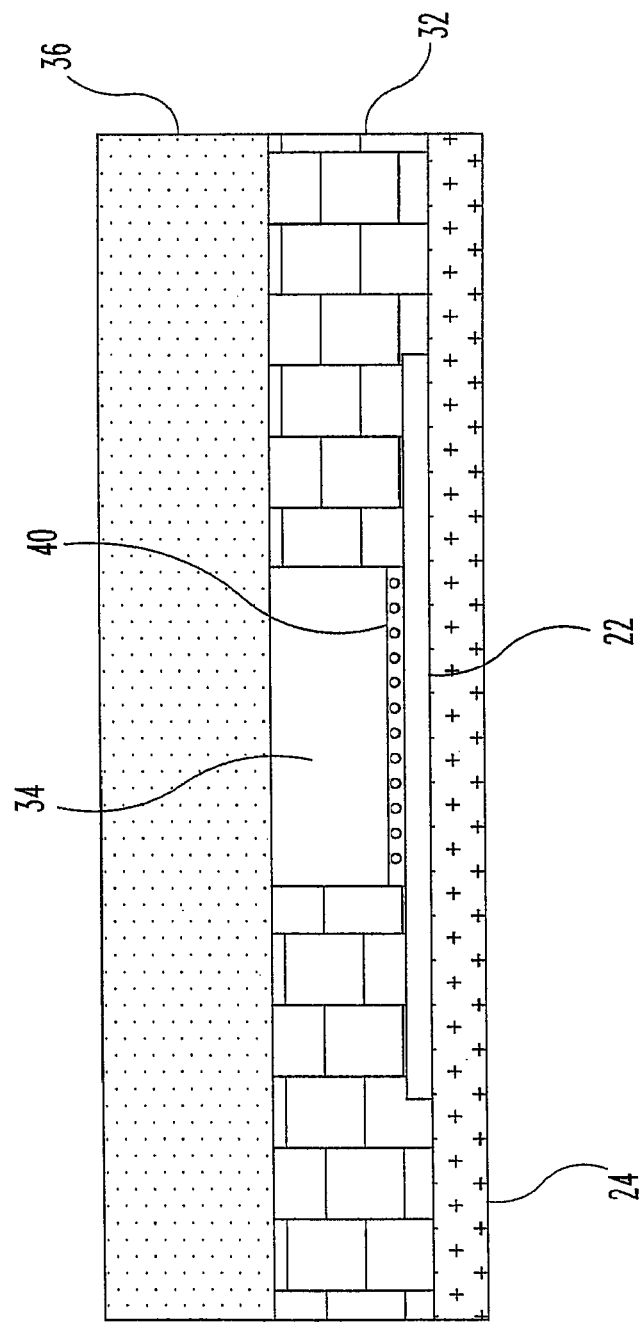
FIG. 5 shows an end view of a sensor of the invention.

FIG. 3 shows different details of a sensor of the invention. FIG. 3 shows sensor 20 comprising flexible substrate 24, an array of interdigitated electrodes 22, and connectors and pads. Non-conductive layer 32 is disposed over the substrate and connector portions 30 of the connectors 26, over portions of the array 22, and not over a rectangular capillary portion including some of the substrate and an intersection of array 22; this rectangular portion defines capillary chamber 34. (A chemical coating, not shown in this figure, is preferably disposed over the array, within the capillary chamber.) Foil 36 covers a rectangular portion of the sensor, including portions of the non-conductive layer 32, and a portion of capillary chamber 34, except for air vent 38. This embodiment is shown from one side in FIG. 4, and from another side in FIG. 5. FIG. 5 specifically illustrates substrate 24, array 22, non-conductive layer 32, which defines chamber 34, and foil 36. FIG. 5 additionally includes coating 40 disposed on array 22, within the capillary.

Figure 6:
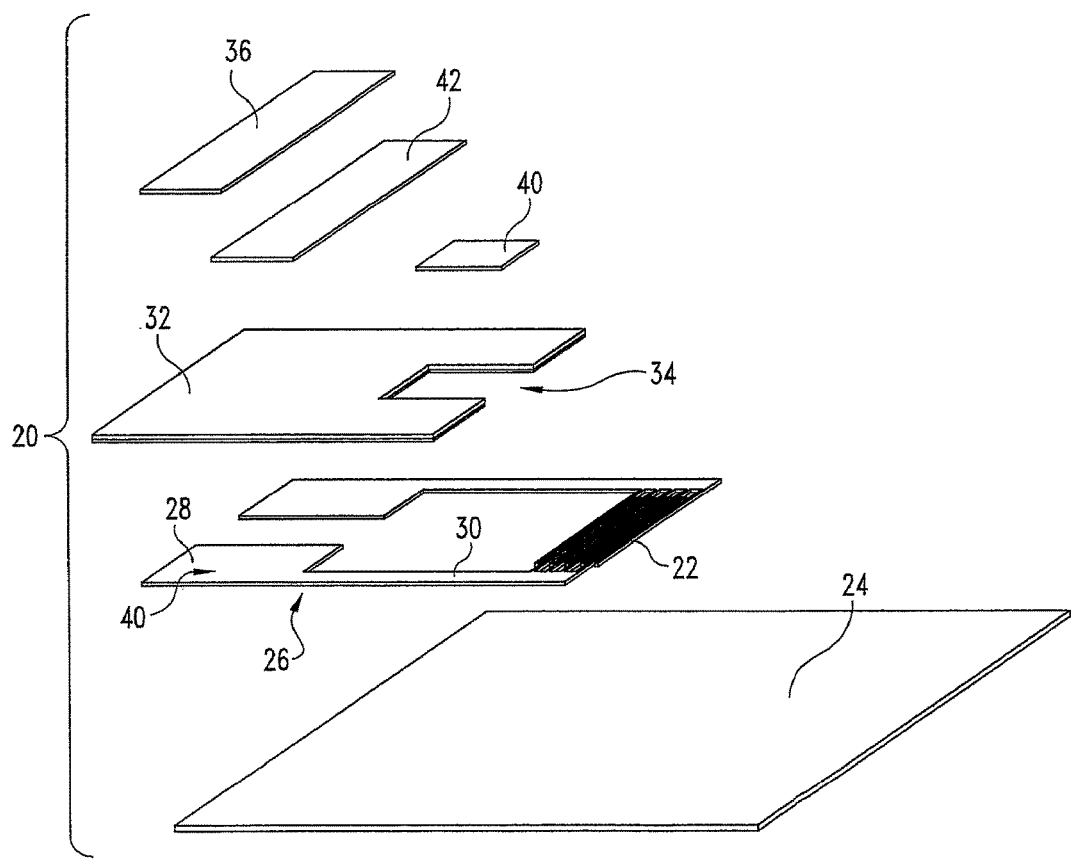
FIG. 6 shows a perspective view of a disassembled sensor of the invention.

FIG. 6 illustrates an exploded view of a sensor of the invention. The sensor 20 includes flexible substrate 24; a conductive film 40 patterned with an interdigitated array of electrodes 22 and connectors 26 which include pad portions 28 and connecting portions 30, an insulating material 32 which defines the depth and dimensions of capillary chamber 34, a chemical coating 40 disposed in the capillary chamber 34, and top foil 36 coated with a hydrophilic adhesive layer 42.

The array of the invention, in various embodiments such as a sensor, can be used in electrochemical detection methods, including those using the principles and specific methods described above, and others. Such methods employ the array disposed on a flexible substrate, preferably further including a chemical coating contacting the array.

Upon contacting the coating with a sample containing analyte, analyte generally diffuses into the coating at a rate dependant on factors such as the chemical composition of the coating and the chemical identity of the analyte. Generally, the chemical coating will be at least partly solubilized or hydrated by the sample substance. For a method to provide the quickest read time (the time following contact with a substance sample, when a reading of the concentration of analyte in the substance is available), it is desirable that the analyte diffuse quickly into the coating, and thereafter quickly and completely react to produce an electroactive reaction product. The period during which this occurs can be reduced by operating on a relatively small volume of sample, and by using a sensor having a relatively small amount of chemical coating to be solubilized or hydrated.

The time from when the substance containing the analyte is contacted with the chemical coating until an assay potential is applied to the array, and during which the analyte diffuses into the coating and reacts to produce an electroactive reaction product, can be referred to as the "delay period". This period can be any amount of time necessary for the above occurrences to transpire, is preferably minimized, and in some embodiments can be less than about 10 seconds, preferably in the range from about 2 to 6 seconds.

After a delay period, the electric properties of the coating can be measured. By chronoamperometric methods, or by potentiometric methods, as will be appreciated by the skilled artisan, either the current or the applied potential can be controlled, and any of the related current, resistance, or voltage can be measured and correlated to amounts of electroactive reaction product and analyte. The magnitude of the current, or alternatively potential difference or the resistance of the chemical coating, can be measured using an external circuit connected to the sensor electrodes.

As an example, according to chronoamperometric methods, a potential ("assay potential") can be applied across the electrodes, inducing a current ("assay current") to flow through the coating. The potential should be enough to cause reduction or oxidation of the redox products formed in the first step of a binary reaction scheme (e.g., as described above), but should not be sufficient to cause other electrochemical reactions or to otherwise cause significant current to flow through the coating. The assay potential can be chosen depending on the redox mediator chosen, factors relating to the electrochemical detection method, the electrochemical system and reaction scheme, and the general capabilities of the sensor. A typical potential can be in the range of a few to several hundred millivolts, e.g., from about 100 to 500, preferably 200 to 400 millivolts.

A measured current can initially exhibit a spike to a relatively elevated level, and can then descend to a steady-state current based on a quasi-steady-state concentration gradients and a recycle reaction loop of the mediator and electroactive reaction product. Preferably, the magnitude of the current can be measured at a time when current flowing through this system has approached a plateau, based on quasi-steady-state concentration gradients. The period of time starting with application of the assay potential and lasting to the plateau or near-steady-state current can be referred to as the "assay period." Steady-state assay currents can occur within various such time periods, depending upon the reaction scheme, the chemistries of its components, etc. In the practice of the invention, assay periods of less than one minute are preferred, e.g., less than 30 seconds, and assay periods of even shorter duration, less than 10 seconds, are most preferred. The assay profile (the profile of the assay current over time) can be to some extent controlled by changing the spacing between electrode elements in the array; increased spacing between electrode elements can result in a longer time interval between assay potential application and formation of the steady state assay currents.

Assay currents exhibited by exemplary sensors of the invention can be any current that will function in an electrochemical detection method. For the sensors of the invention, any useful current can be used, preferably with a range between a lower end in the nanoamp range (e.g., between 20 to 25 nanoamps) up to the microamp range e.g., 100 microamps, being an exemplary working range, e.g., at the steady state current plateau. Typical steady state assay currents can be in the range from below one microamp up to around 100 microamp, preferably from about 0.5 to about 25 microamps. In an embodiment of the invention useful for detecting glucose content of a blood sample, the current response (steady state assay current) in this range has been found to be linear with respect to the concentration of glucose in the sample, particularly for glucose concentrations in the range from about 0 to 600 milligrams per deciliter (mg/dL).

As recited above, the present invention can be applied to known electrochemical methods described in U.S. Pat. No. 5,128,015 and European Patent Specification 0 406 304 B1. Accordingly, the present invention can be used to measure the concentration of glucose in a blood sample by adding the blood sample to a chemical reagent that includes an enzyme and a mediator (an electron acceptor, such as benzoquinone or ferricyanide). Following an open circuit delay period, an assay potential can be applied to measure assay current, wherein at the time the assay current is measured the assay current is decaying proportionally to $t^{-0.5}$, wherein t is time measured from the beginning of application of the assay potential. This assay current can be correlated to the concentration of glucose in the blood sample.

Sensors of the invention may be used in cooperation with electronic or computerized systems and apparatuses, and in combination with methods for identifying analytes and measuring concentration of analytes within a substance sample. For example, a sensor can be used with a VXI or Biopotentiostat test stand built from components purchased from National Instrument Corp., Austin, Tex. In this context, the method of the invention can be practiced with a delay period of around 3 seconds, an assay potential of about 300 millivolts, and an assay period which, although variable, can preferably be in the range from about 1.5 to 2 seconds after applying the assay potential.

The sensors can be used in such a method to detect and quantify the concentration of an analyte within a sample substance. The analyte can be chosen from various chemical compounds present within any of a large variety of substances, generally fluids. Examples of analytes include glucose, cholesterol, urea, and the like. Examples of substances containing the analyte include bodily fluids such as blood, urine, and interstitial fluid; water such as environmental water, ground water, waste water, etc.

In some embodiments of the invention, analytes can be detected at very low concentrations, for example glucose can be measured at concentrations as low as 0.5 mg/dL (5 ppm) in blood using ferricyanide as the mediator.

The use of an array or sensor of the invention offers certain practical advantages. For instance, a flexible substrate can be used in combination with relatively larger-dimensioned electrodes, including electrode components of increased size (e.g., width) as well as increased spacing between them. Lower sample volumes can independently decrease the time of the delay period. A shorter delay period in combination with an expedited formation of a quasi-steady-state region of the assay current produces a quicker read time. In the practice of the invention, read times of less than 10 seconds have been achieved, with read times in the range from about 4 to about 5 seconds being preferred.

Test cells and test strips according to the invention allow for controlled volumes of blood to be analyzed without pre-measuring. Insertion of the test cell into an electronic or computer-controlled apparatus (referred to generally as a test stand) permits automatic functioning and timing of the reaction and analysis of the sample. This allows for patient self-testing with a very high degree of precision and accuracy. The method, the sensor or test cell, and the apparatus, are designed to provide self-monitoring by a patient of important bodily fluids, e.g., blood glucose levels. The sensor is used to control the sample volume and reaction media, to provide precise, accurate, and reproducible analysis. Preferably, disposable test strips or test cells can be used in combination with a portable electrochemical testing meter.

The preferred embodiment of the present invention uses a micro-electrode array consisting of interdigitated microband electrodes as described above. Although this arrangement leads to the aforementioned re-cycling of redox products between narrowly separated working and counter electrodes, this is not a strict requirement for successful practice of the invention. An alternative embodiment is the provision of an array of more general micro-electrodes to act as the working electrode structure. These may be microbands that are not interdigitated with the counter electrode, or micro-disks, also not closely spaced with the counter electrode. In this case the width or diameter of the working electrode bands or disks should be of such a dimension as to allow for some degree of radial or spherical diffusion to the working electrode surfaces. Typically, this dimension should be in the range of 5 to 50 µm, and most preferably 10 to 50 µm for the case of aqueous systems such as encountered with a sensor used for the assay of biological fluids. In both cases the counter electrode is provided at a distance from the working array that is generally larger than the smallest dimension of the working electrodes.

In these embodiments, specific recycling of redox species between the working and counter electrodes is not observed in the same way as in other described embodiments, and assay current magnitudes are consequently reduced. Nevertheless, the effect of radial or spherical diffusion to working micro-electrode structures can still be observed as current densities that are greater than that predicted from linear diffusion alone. Although reduced in magnitude, and not approaching quasi-steady-state as displayed by the preferred embodiments, it is still possible to measure dose responses to the analyte in question (e.g. glucose) when the same reagent as described above is disposed on the micro-electrode array.

Micro-electrode arrays of the invention can be disposed onto a flexible substrate using various methods useful for disposing electronic components onto substrates, especially flexible substrates. A variety of such methods are generally known for fabrication of different types of circuitry, and include specific techniques of dry-coating, lamination, spin-coating, etching, and laser ablation. One or more of the following generalized methods may be specifically useful to prepare microelectrode arrays according to the invention.

A chemical coating may also be disposed onto the array. First, however, it may be beneficial to clean the sensors. By one cleaning method, a sheet of sensors as described can be plasma cleaned in a Branson/IPC Plasma Cleaner according to steps such as the following: (1) $O_2$ for 1 minute at 800 watts; (2) $O_2$/Argon(Ar) (70/30) for 3 minutes at 220 watts; (3) Ar for 2 minutes at 150 watts.

A chemical coating, as described, may be dispensed onto the array, e.g., into each capillary chamber and over the interdigitated arrays, by known methods. The method of dispensing is preferably capable of reproducibly and consistently delivering very small volumes of a chemical composition, onto the array—e.g., volumes in the range of hundreds of nanoliters, e.g., 625 nanoliters. As an example, such a coating may be dispensed using known syringe and metering techniques and apparatuses, including dispensing systems sold under the trade name Microdot (from Astro Dispense Systems, a DCI Company of Franklin, Mass. 02038-9908) and systems sold by BioDot Inc., Irvine, Calif. The coatings may then be dried of solvent. The inlet ports are opened, and a top foil coated with a hydrophilic adhesive is applied over the capillary chamber using heat and pressure to form the completed three-dimensional sensor structure.

EXAMPLE 1

The following describes a process useful for preparing a sensor according to the invention, comprising an interdigitated array disposed on a flexible substrate. According to the method, a gold film can be deposited onto 7 mil thick Kaladex® film using a planar DC magnetron sputtering process and equipment, from Techni-Met Inc., Windsor, Conn. The thickness of the gold film can range from 30 to 200 nm, with a preferred thickness being 100 nm. Seed layers of chromium or titanium can be sputtered between the plastic film and the gold to promote better adhesion of the gold to the plastic substrate, however, gold layers sputtered directly onto the plastic film can exhibit sufficient adhesion.

The interdigitated array and connectors can be fabricated using batch photolithography processes common to the flex circuit industry. Electrodes with combinations of finger width and spacing between fingers in the range of 21 to 50 um were easily fabricated using these processes. A preferred configuration of the array was 21 total fingers (10 working electrode fingers and 11 counter electrode fingers), with finger dimensions of 25 microns (width) by 1 millimeter (length), with 21 micron spacing between the fingers.

Sensor chambers were fabricated using dry film photoimageable coverlay materials such as that sold under the trademark Vacrel® 8140 (duPont) or Pyralux® PC series (duPont). The chamber dimensions can be accurately defined by flex circuit photolithography. Depth of the chamber was controlled by the thickness of the coverlay materials used, and whether single or multiple layers of the coverlay dry film were used. A preferred chamber depth was 125 microns (5 mil). This chamber depth was achieved by sequential lamination of different coverlay materials as follows: three mil thick Vacrel® 8130 was first laminated to the electrode side of the substrate using a HRL-24 (duPont) heated roll laminator at room temperature, using a roller speed of 1 meter per minute. The electrode panel was then vacuum laminated in a DVL-24 vacuum laminator (duPont) using settings of 120° F., 30 second vacuum dwell, and a 4 second pressure to remove entrapped air between the coverlay film and the electrode substrate. Two mil thick Vacrel 8120 was laminated next to the Vacrel® 8130 surface using the HRL-24 at room temperature, with a roller speed of 1 meter/min. The panel was then vacuum laminated again in the DVL-24 vacuum laminator using a 30 second vacuum dwell, 4 second pressure, to remove entrapped air between the two coverlay films.

The laminated electrode sheet was placed in the Tamarack 152R system and was exposed to ultraviolet light at 365 nm through the photomask for 22 seconds using an exposure intensity of 17 mW/cm$^2$. The artwork for the capillary chamber was a 1 millimeter by 4 millimeter rectangle centered over the electrode finger array and starting 1 millimeter below the fingers. The exposed coverlay was stripped from the panel to reveal the sensor chamber rectangle using the VLP-20 Circuit Chemistry Equipment) in 1% $K_2CO_3$, at 140° F., for 75 seconds using a nozzle pressure of 34 psi. The developed laminate structure was rinsed in deionized water, and then cured at 160° C. for 1 hour to thermally crosslink the coverlay material. This completed the construction of the sensor base.

The chemical coating was formulated for measurement of d-glucose in a human blood sample. The chemical coating was reactive with the sample in a manner effective to generate an electrical output signal indicative of the level of glucose in the sample. The coating included a mediator, enzymes, and a cofactor. The coating further comprised film forming agents and detergents conferring durability and providing hydrophilicity. The ingredients are listed in Table 1; unless stated otherwise, all concentrations refer to the concentration of a given substance in a wet-coating, prior to the deposition and drying of the coating onto the array.

The hydrophilic top foil was prepared by coating an adhesive mixture (e.g., a mixture of Fastbond™ 30-NF Contact Adhesive and the surfactant Triton™ X-100 (Union Carbide, Danbury Conn.), 93%:7% wt/wt.) to a wet thickness of 25 um onto 5 mil polyester film such as that sold under the trademark Melinex® "S" (duPont Polyester Films, Wilmington Del.) using a wire bar coater from Thomas Scientific, Swedesboro, N.J. The coated top foil was dried for 2 minutes at 50° C. in a horizontal air flow oven (VWR Scientific Products). The capillary chamber was opened by cutting 1 millimeter in from the front edge of the capillary chamber with a pair of scissors. The dried coated top foil was applied to the sensor, allowing approximately a 0.5 mm space between the back edge of the chamber and the edge of the top foil as an air vent. The top foil was sealed to the sensor surface using a 5 ton press with a heated top platen, at 81° C., 60 psi for 5 seconds. The panel of completed sensors was cut into individual sensors and stored desiccated at 8% RH until tested.

The sensors were evaluated using chronoamperometry electrochemical techniques on test stands such as that sold under the trademark of BAS™ 100 W Electrochemical Workstation, Bioanalytical Systems, Inc. West Lafayette, Ind. The preferred electrochemical test stand used in the evaluation of the electrodes was a dedicated test stand for DC chronoamperometric current measurement for assay potentials from ±1 volt.

The sensors may be used to determine the concentration of an analyte, such as glucose, in a fluid sample by performing the following steps:

Set Up the Test Stand Parameters:

In accordance with a "drop detect" system, an initial potential difference is established between the working and counter electrodes—300 mV (millivolts)—to start timing of the analysis sequence. Current response to this potential is triggered by contact of the array with a fluid sample.

The initial current response upon application of the test solution to the sensor chamber is generally greater than 0.4 microamps.

The time (delay period) between the threshold trigger and re-application of the 300 mV potential difference (assay potential) is generally 3 seconds.

The assay period, after re-application of the 300 mV potential difference between the working and counter electrodes of the sensor is generally 9 seconds.

In More Detail:

Insert the sensor into the test stand connection. Apply approximately 0.3 uL of a fluid sample to the opening of the capillary chamber. Fluid will flow into the chamber by capillary action covering the chemical coating applied to the working and counter electrodes. The threshold current will be triggered when the sample fluid covers the nearest working and counter electrode fingers. Once triggered, the potential difference will go to open circuit for a 3 seconds, during the delay period.

During the delay period, reaction will occur between the reactants (analyte, enzyme/cofactor, and the oxidized form of the mediator), resulting in reduction of the mediator.

The 300 mV assay potential difference is re-applied between the electrodes after the 3 second delay. This causes electro-oxidation of the reduced mediator at the surface of the working electrode.

Figure 7:
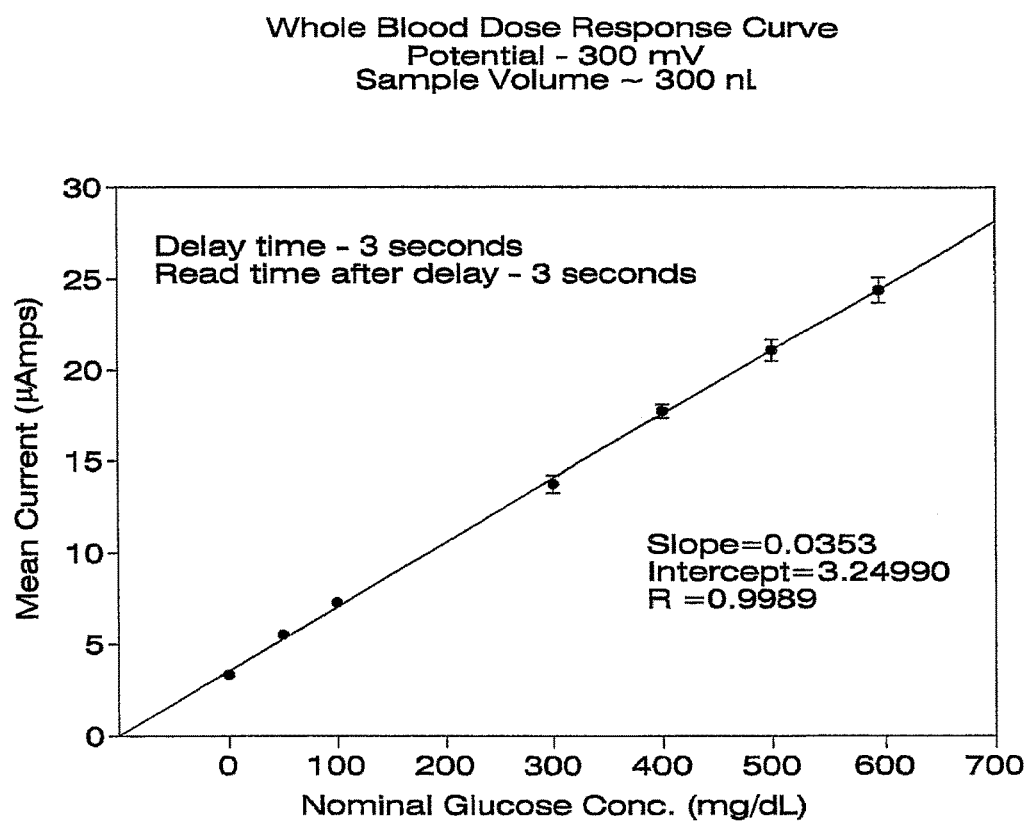
FIG. 7 shows a dose response plot of assay current versus blood glucose level.

The current/time reaction profiles of the assay show a characteristic pseudo-steady-state current/time plateau starting 0.5 to 1.5 seconds after re-application of the 300 mV assay potential to the sensor. Currents at fixed assay period points chosen in this plateau region were proportional to the concentration of analyte in the sample fluid. Assay endpoints were chosen in such a manner give a linear dose response for glucose concentrations from 0 to 600 mg/dL. See FIG. 7.

EXAMPLE 2

A sensor having an interdigitated array of two electrodes configured for 57 fingers (27 fingers for the working electrode and 28 fingers for the counter electrode) was initially prepared by depositing gold film onto a KALADEX® substrate according the procedure described in Example 1. Each finger of the working electrode and the counter electrode had a width of 50 microns (μm) and was separated from the adjacent finger by a 21 μm gap. The sensor chamber or capillary was fabricated into a coverlay of Vacrel® 8140 material using dry film photolithography. The capillary or chamber had a depth of 0.125 mm and a sample volume of 1.45 μl.

The hydrophilic top foil was prepared by coating an adhesive mixture (e.g., an adhesive mixture of 4.5% TRITON X100®, 4.5% isocyanate (38-8569 from National Starch and Chemical Co. of Bridgwater, N.J.), and 93% polyurathane (38-8668 also from National Starch and Chemical Co.) to a wet thickness of 25 μm onto 5 mil film of Melinex® "S" (duPont Polyester Films, Wilmington Del.) using a wire bar coater from Thomas Scientific, Swedesboro, N.J. The coated top foil was dried for 2 minutes at 50° C. in a horizontal air flow oven (VWR Scientific Products). The capillary chamber was opened by cutting 1 millimeter in from the front edge of the capillary chamber with a pair of scissors. The dried coated top foil was applied to the sensor, allowing approximately a 0.5 mm space between the back edge of the chamber and the edge of the top foil as an air vent. The top foil was sealed to the sensor surface using a 5 ton press with a heated top platen, at 81° C., 60 psi for 5 seconds. The panel of completed sensors was cut into individual sensors and stored desiccated at 8% RH until tested.

The chemical formulations were also prepared as described in Example. 1 (See Table 2). The chemicals were applied to the sensor chamber at a discrete dispense volume of 1.226 μl into the 2 mm×5.8 mm chamber for each sensor. The resulting sensor had a sample volume of 1.5 μl.

The series of sensors prepared as above described were evaluated by measuring the current across the electrodes produced from a series whole blood test samples spiked with glucose and Hct at varying concentrations. The percentage of Hct and actual glucose concentrations in the test samples are listed below in Table 3.

TABLE 3

| Nominal Glucose | Actual Glucose Concentration at various Hematocrit (Hct) levels (mg/dl) | | | | |
|---|---|---|---|---|---|
| Conc. mg/dL | 20.0% Hct | 30% Hct | 45% Hct | 60% Hct | 70% Hct |
| 50 | 51.7 | 46.54 | 38.19 | 25.78 | 17.01 |
| 100 | 128.38 | 121.12 | 111.64 | 103.33 | 92.65 |
| 200 | 201.37 | 194.21 | 198.10 | 188.76 | 183.44 |
| 400 | 419.79 | 418.72 | 414.27 | 409.85 | 405.86 |
| 600 | 622.30 | 612.72 | 613.76 | 609.89 | 593.29 |

The procedure employed for the evaluation is the same as described in Example 1. The test parameters included a time (delay period) between the threshold trigger and re-application of the 300 mV (dc) potential difference (assay potential) of 3 seconds. Data was collected immediately after the delay period at 4 data points per second for an assay period of about 9 seconds.

Figure 8:
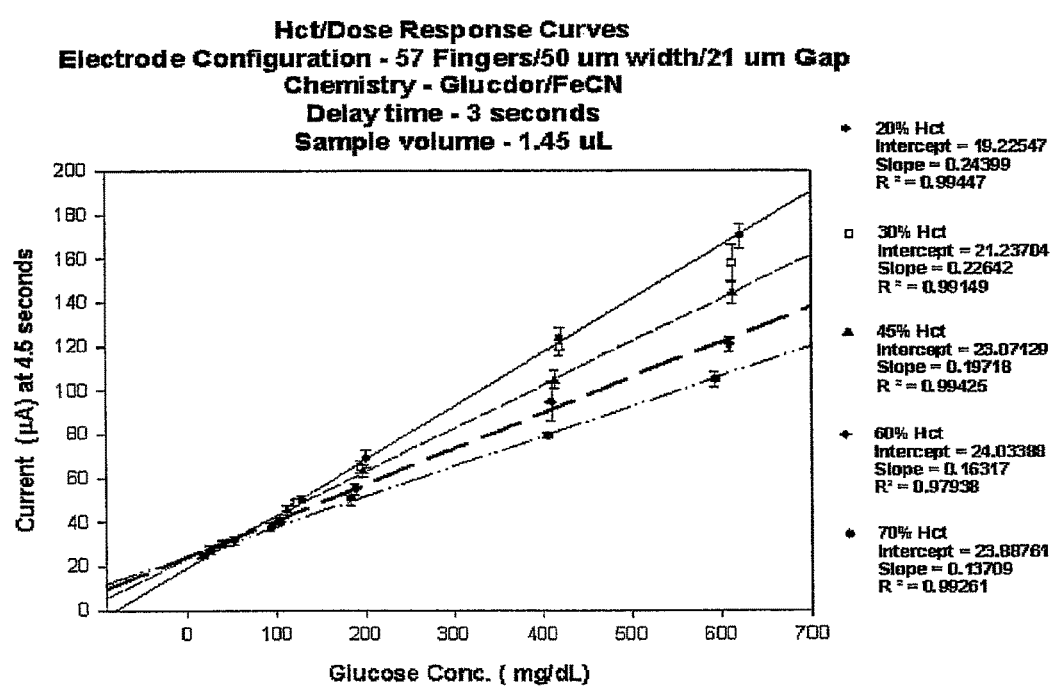
FIG. 8 shows a Hct/dose response plot for glucose collected at 4.5 seconds after dose detection.

The results are illustrated in FIG. 8. The current/time profiles of the assay were consistent with a characteristic pseudo-steady state current/time plateau at least at 4.5 seconds after dose detect (1.5 sec after reapplication of the 300 mV assay potential to the sensor.) The assay provided linear dose responses for varying glucose concentrations at each of the different Hct levels, with a correlation coefficient ($r^2$) of greater than 0.979.

EXAMPLE 3

Sensors were prepared according to this method by depositing a gold film onto a flexible substrate as described in Example 1. After the gold was applied to the flexible substrate, a spin on photoresist was applied according to the procedure described in Linder et al. "Flexible Kapton-Based Microsensor Arrays of High Stability for Cardiovascular Applications," *J. Chem. Faraday Trans.* 1993, 89(2), 361-367; Cosofret et al. "Microfabricated Sensor Arrays Sensitive to pH and K+ for Ionic Distribution Measurement in the Beating Heart" *Anal. Chem.* 1995, 67, 1647-1653. The photoresist, (Microposit Shipley 1813 from Shipley of Marlborough Mass.) was spun on to a flexible Kaladex® substrate at 4,000 rpm for 4 seconds. The coated substrate was baked at 90° C. for 15 minutes. The photoresist was exposed through a photomask to uv light at 15.5 mW/cm$^2$ for 11 seconds. The photomask was patterned to provide the electrodes with a hook configuration as illustrated in FIG. 9. The coated substrate was heated to 115° C. for 15 minutes. The photoresist was developed to remove the area exposed to the uv light. The exposed gold was removed with iodide/potassium iodide/water (4:1:40) bath. The photoresist was stripped from the laminated substrate with an acetone/methanol solution. The resulting patterned gold substrate was then dried at 120° C. for 30 minutes. The working electrode had a surface area of 1 mm$^2$ (1 mm×1 mm); the counter electrode had dimensions of 600 mm length, 2.6 mm+1.8 mm+1.8 mm width). The electrodes were separated by a 200 μm gap.

The resulting substrate was laminated with PYRALUX® PC 1000. The laminated substrate was exposed to uv light at 15.5 mW/cm$^2$ through a photomask for 11 seconds. The exposed coverlay was developed with a $LiCO_3$ solution and then thermally cured at 160° C. for 60 minutes. The coverlay was fabricated to have a capillary or chamber with a depth of 0.062 mm. The resulting "box hook" sensor had a test sample volume of 0.775 μl.

The sensor was cleaned to remove any residual photoresist and coverlay material. A chemical coating formulation was prepared as described in Example 1. The components and their amounts are listed below in Table 4.

TABLE 4

| Formulation per 100 grams of coating | | | |
|---|---|---|---|
| Component | Concentration/ activity | Wet mass (g) | Dry mass/sensor (mg) |
| Distilled Water | | 89.51 | |
| Potassium monophosphate | | 1.2078 | 0.0121 |
| | | 2.7133 | 0.0271 |
| Potassium diphosphate Buffer | 150 mM pH 7.00 | | |
| Trehalose | 0.35% wt/wt | 0.350 | 0.0035 |
| Natrosol 250 M | 0.060% wt/wt | 0.060 | 0.0006 |
| Polyethylene oxide (100K) | 0.750% wt/wt | 0.750 | 0.0075 |
| Triton X-100 | 0.070% wt/wt | 0.070 | 0.0007 |
| Pyrrolo-quinoline-Quinone (PQQ) | 0.315 mM | 0.0104 | $1.040 \times 10^{-5}$ |

TABLE 4-continued

Formulation per 100 grams of coating

| Component | Concentration/ activity | Wet mass (g) | Dry mass/sensor (mg) |
|---|---|---|---|
| GlucDor Enzyme | 2624 u/mg (DCIP) | 1.1325 | 0.0113 29.717 units |
| Potassium Ferricyanide | 179.4 mM | 5.908 | 0.0591 |

A sheet containing several sensors was prepared according to the procedure above described. The sheet was cut to isolate the individual sensors. Lines were drawn on each side of the sensor chamber using a black Sharpie marking pen to define the reaction area for chemistry dispensing. The reagent coating was hand dispensed at a discrete dispense volume of 1.0 µl into the 2.5 mm×5.0 mm chamber for each sensor.

A series of sensors prepared as above described were evaluated by measuring the current generated across the electrodes produced for a series of test samples having differing concentrations of glucose according to the procedure described in Example 1. The test parameters included a time (delay period) between the threshold trigger and re-application of the 300 mV (dc) potential difference (assay potential) of 4 seconds. Data was collected immediately after the delay period at 4 points per second generally for an assay period of 9-12 seconds.

Figure 10:
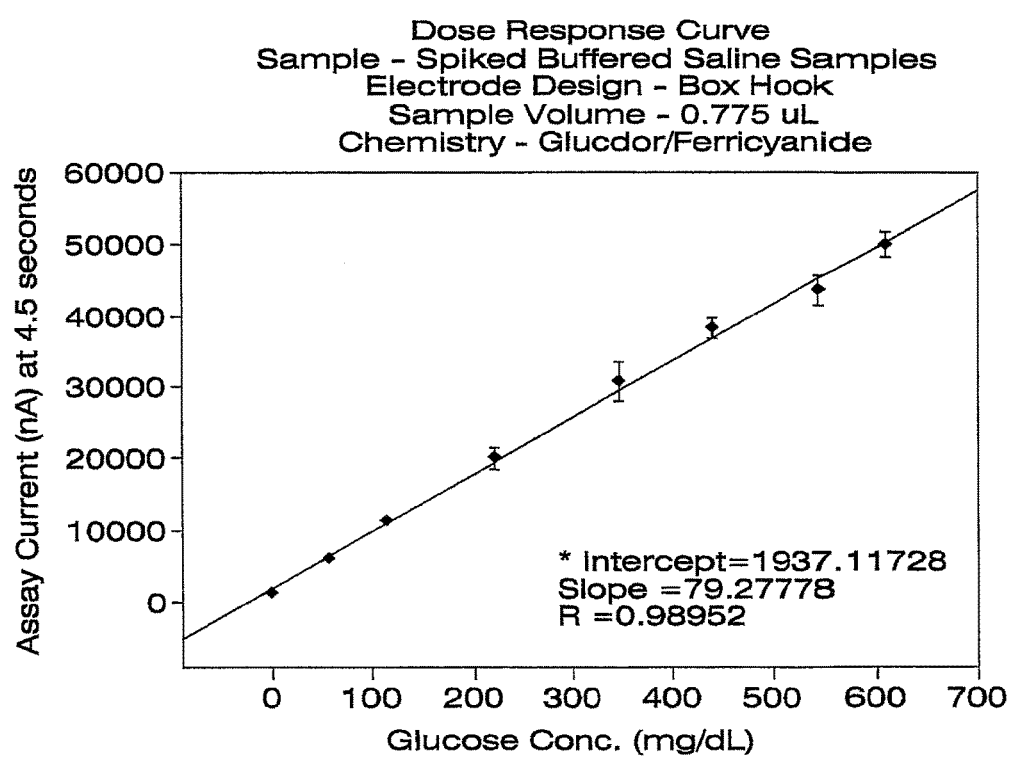
FIG. 10 shows a dose response plot for glucose spiked saline samples collected at 4.5 seconds after dose detection.

An assay point was chosen from the current/time profiles of the assay at 4.5 sec. after dose detect (0.5 sec after reapplication of the 300 mV assay potential to the sensor. The results are illustrated in FIG. 10. The assay provided a linear dose response for the different glucose levels, with a correlation coefficient ($r^2$) of 0.990.

EXAMPLE 4

A sensor having an interdigitated array of two electrodes and 3 fingers (1 working electrode finger and 2 counter electrode fingers) was initially prepared according the procedure described in Example 3. The electrodes were gold film. Each working electrode finger had a width of 500 µm, and each of the counter electrodes had a width of 500 µm. The electrode array had a gap of 150 µm between the fingers of the working electrode and the adjacent counter electrode. The capillary or chamber was fabricated to have a depth of 0.062 mm and a sample volume of 0.620 µl.

The chemical formulations were also prepared as described in Example 3 (See Table 3). The reagent coating was applied to the sensor chamber at a discrete dispense volume of 1.00 µl into the 2 mm×5.0 mm chamber for each sensor.

A series of sensors prepared as above described were evaluated by measuring the current generated across the electrodes produced for a series of test samples having differing concentrations of glucose to the procedure described in Example 1. The test parameters included a time (delay period) between the threshold trigger and re-application of the 300 mV (dc) potential difference (assay potential) of 4 seconds. Data was collected immediately after the delay period at 4 data points per second generally for an assay period of about 9 seconds.

Figure 11:
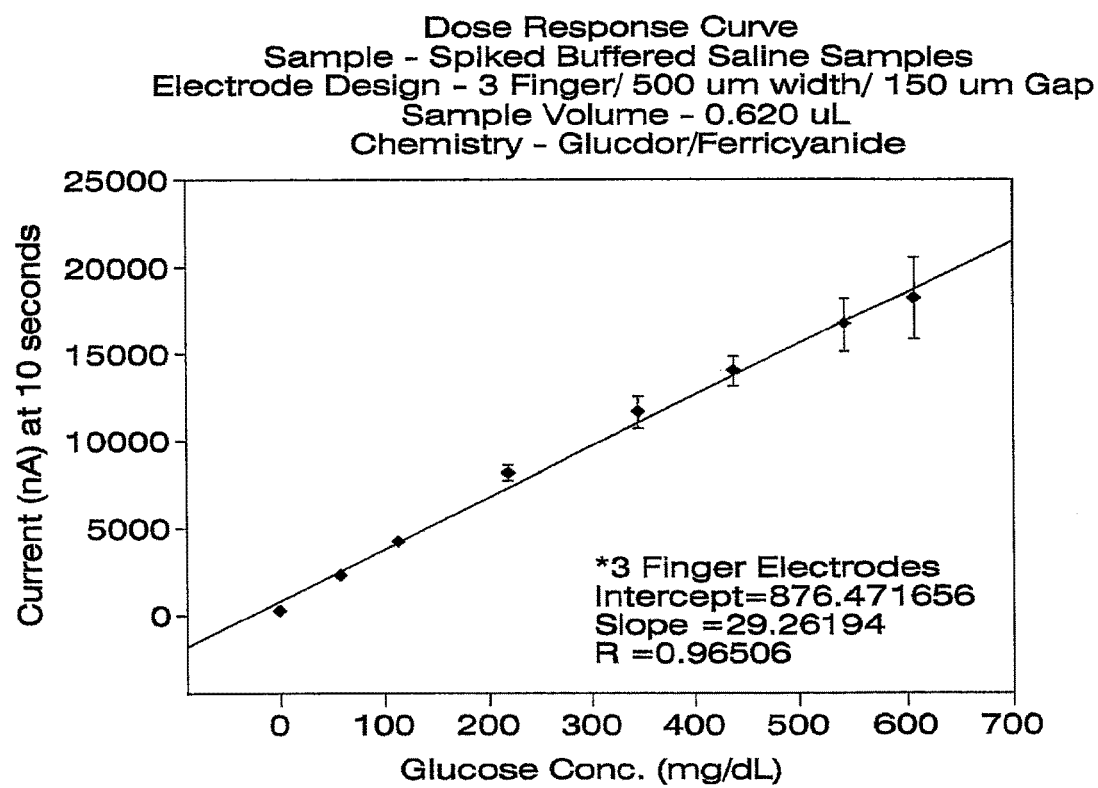
FIG. 11 shows a dose response plot for glucose spiked saline samples collected at 10 seconds after dose detection.

An assay point was chosen from the current/time profiles of the assay at 10 sec. after dose detect (6 sec after reapplication of the 300 mV assay potential to the sensor. The results are illustrated in FIG. 11. The assay provided a linear dose response for varying glucose concentrations, with a correlation coeffecient ($r^2$) of 0.965.

EXAMPLE 5

A sensor having an interdigitated array of two electrodes and 5 fingers (2 working electrode fingers and 3 counter electrode fingers) was initially prepared according the procedure described in Example 3. The electrodes were gold film. Each finger of the working electrode had a width of 300 µm, and each finger of the counter electrode had a width of 300 µm. The electrode array had a gap of 300 µm between the working electrode fingers and the counter electrode fingers. The capillary or chamber was fabricated to have a depth of 0.062 mm and a sample volume of 0.620 µl.

The chemical formulations were also prepared as described in Example 3 (See Table 3). The reagent coating was applied to the sensor chamber at a discrete dispense volume of 1.00 µl into the 2 mm×5.0 mm chamber.

A series of sensors prepared as above described were evaluated by measuring the current generated across the electrodes produced for a series of test samples having differing concentrations of glucose according to the procedure described in Example 1. The test parameters included a time (delay period) between the threshold trigger and re-application of the 300 mV (de) potential difference (assay potential) of 4 seconds. Data was collected immediately after the delay period at 4 data points per second generally for an assay period of about 9 seconds.

Figure 12:
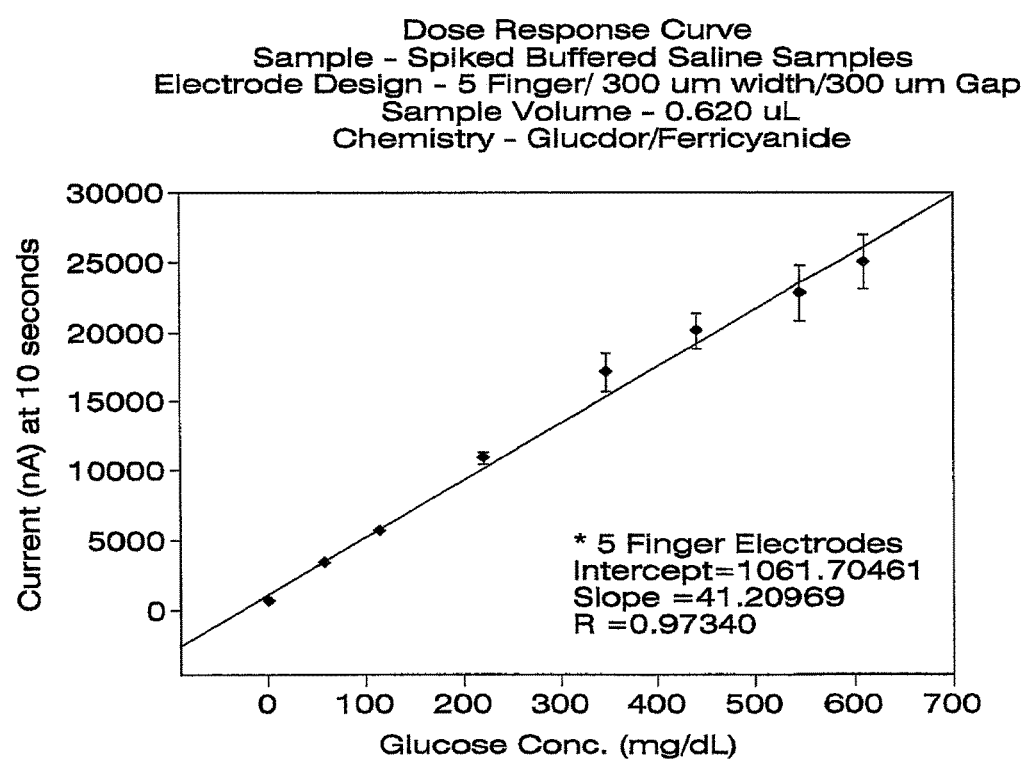
FIG. 12 shows a dose response plot for glucose spiked saline samples collected at 10 seconds after dose detection.

An assay point was chosen from the current/time profiles of the assay at 10 sec. after dose detect (6 sec after reapplication of the 300 mV assay potential to the sensor. The results are illustrated in FIG. 12. The assay provided a linear dose response for the different glucose concentrations, with a correlation coeffecient ($r^2$) of 0.973.

EXAMPLE 6

A sensor having an interdigitated array of two electrodes and 29 fingers (14 working electrode fingers and 15 counter electrodes fingers) was initially prepared according the procedure described in Example 2. The electrodes were gold film. Each finger of the working electrode had a width of 50 µm, and each finger of the counter electrode had a width of 50 µm. The electrode array had a gap of 25 µm between the fingers of working electrode and the adjacent finger of the counter electrode. The capillary or chamber was fabricated to have a depth of 0.127 mm and a sample volume of 1.02 µl.

The coverlay material was prepared by laminating two layers of PYRALUX® PC 1000.

The chemical formulations were also prepared as described in Example 2 (See Table 3). The chemicals were applied to the sensor chamber at a discrete dispense volume of 1.00 µl into the 2 mm×5.0 mm chamber.

A series of sensors prepared as above described were evaluated by measuring the current generated across the electrodes produced for a series of test samples having differing concentrations of glucose at various Hct levels according to the procedure described in Example 1. The actual glucose concentration of each sample was determined as listed in Table 5.

TABLE 5

| Nominal Glucose Concentration | Actual Glucose Conc. at various Hematocrit (Hct) levels (mg/dl) | | | | |
|---|---|---|---|---|---|
| mg/dL | 0.0% | 20% | 40% | 55% | 70% |
| 0 | 0.0 | 0.0 | 0.0 | 0.0 | 0.0 |
| 50 | 48.5 | 47.2 | 45.15 | 40.70 | 42.85 |
| 100 | 94.75 | 94.75 | 92.25 | 91.30 | 81.60 |
| 300 | 290.75 | 291.5 | 289.2 | 276.85 | 294.20 |
| 600 | 575.05 | 569.15 | 574.95 | 548.55 | 555.0 |

The test parameters included a time (delay period) between the threshold trigger and re-application of the 300 mV (dc) potential difference (assay potential) of 2 seconds. Data was collected immediately after the delay period at 20 data points per second generally for an assay period of about 9 seconds.

Figure 13:
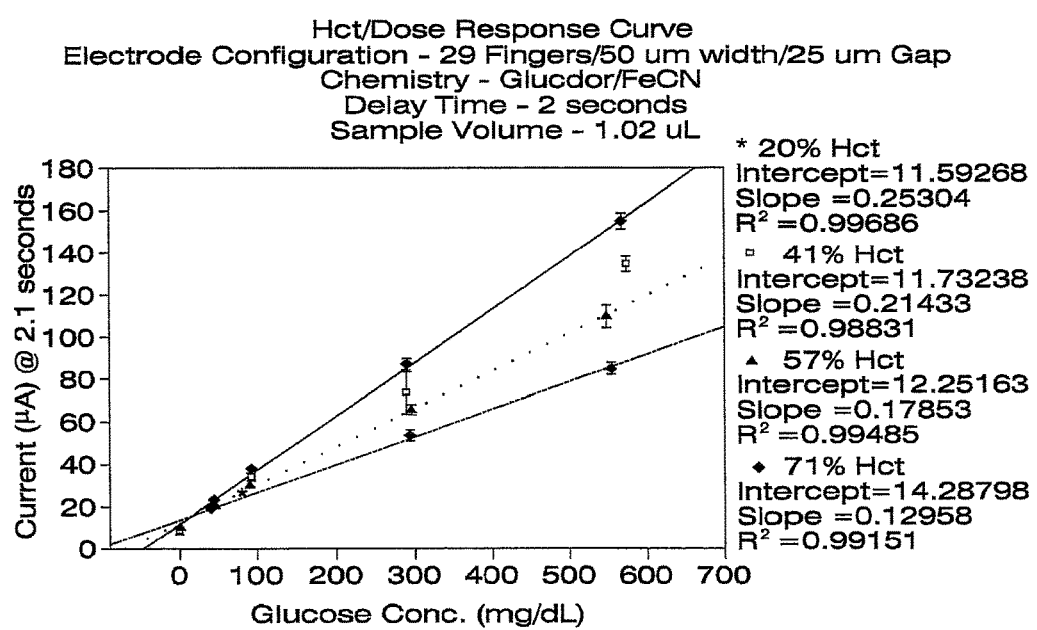
FIG. 13 shows a Hct/dose response plot for glucose spiked whole blood samples collected at 2.1 seconds after dose detection.
Figure 14:
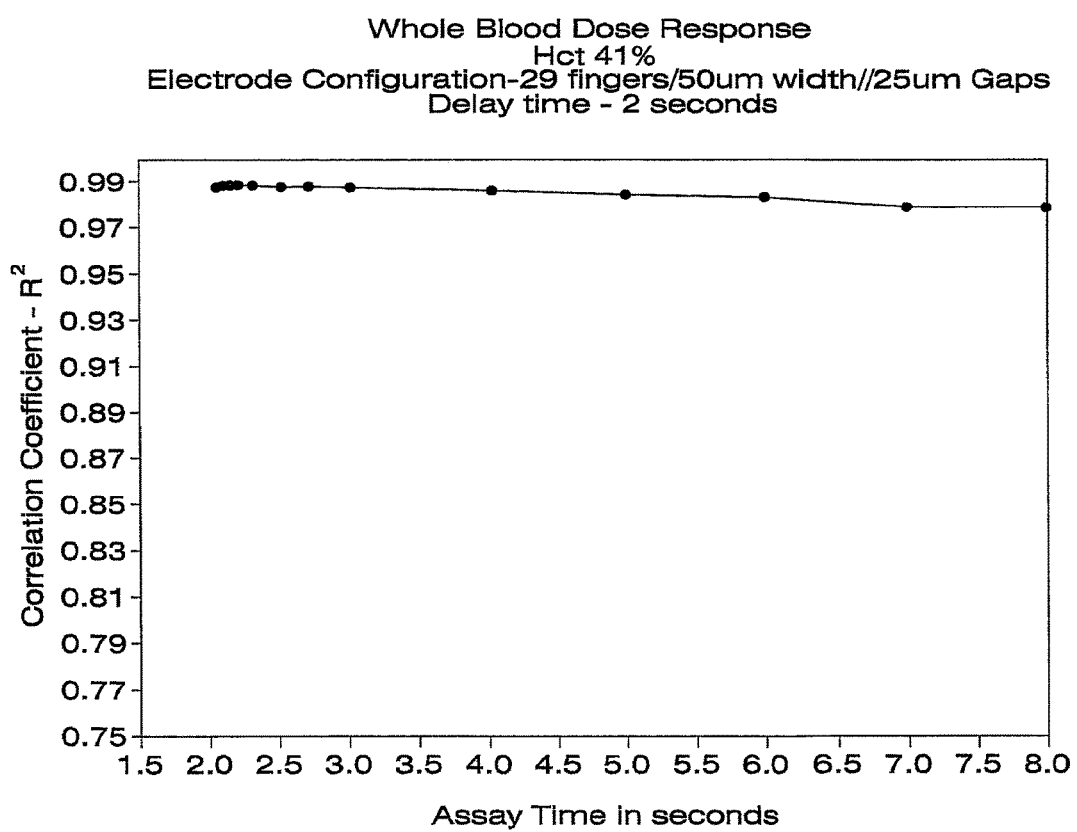
FIG. 14 shows a plot of the correlation coefficient ($r^2$) versus assay time for the data collected in FIG. 13 and for various other Assay Times.

The results are illustrated in FIG. 13. An assay point was selected from the current/time profiles of the assay at 2.1 seconds after dose detect (0.1 seconds after reapplication of the 300 mV assay potential to the sensor. The assay provided a linear dose response for varying glucose concentrations at different Hct levels, with a correlation coeffecient ($r^2$) of greater than 0.988 (See FIG. 14).

What is claimed is:

1. A method of analyzing an analyte in a biological fluid sample, the method comprising:
    providing an electrochemical sensor comprising:
        a flexible substrate;
        a conductive pattern disposed on the flexible substrate, the conductive pattern comprising:
            an interdigitated array comprising first and second, electrodes electrically isolated from each other, the first electrode comprising first electrode elements electrically connected to a first common element, the second electrode comprising second electrode elements electrically connected to a second common element the number of first electrode elements being one more or one less than the number of second electrode elements;
            first and second pads and first and second connectors electrically connecting the first and second pads to the first and second electrodes, respectively;
            wherein each electrode element comprises a width of about 50 micrometers, and wherein the electrode elements of the first electrode are spaced substantially equally from the electrode elements of the second electrode by gaps, each gap having, a distance of about 25 micrometers;
        a chemical coating disposed over at least a portion of the first electrode, the chemical coating configured for reacting with an analyte to produce an electroactive reaction product; and
        a capillary chamber overlying at least a portion of the interdigitated array and configured to direct flow of a biological fluid sample into contact with the chemical coating on the first electrode, the capillary chamber having a volume from about 250 nanoliters to about 400 nanoliters;
    contacting the capillary chamber with a biological fluid sample, the capillary chamber directing the biological fluid sample into contact with the first and second electrodes and the chemical coating to at least partly solubilize or hydrate the chemical coating;
    detecting the contacting of the first and second electrodes by the biological fluid sample and starting a delay period of about 2 seconds allowing the analyte and chemical coating to react and to produce electroactive reaction product;
    after the delay period, starting an assay period by applying an assay potential across the first and second electrodes for inducing an assay current across the electrodes resulting from oxidation of the electroactive reaction product at one of the first and second electrodes, the assay current reaching a steady-state current;
    measuring a magnitude of the assay current during the assay period after the assay current has reached the steady-state current, the measuring step being performed beginning about 2.1 seconds after the start of the delay period; and
    correlating the magnitude of the assay current to a concentration of the analyte in the biological fluid sample.

2. The method of claim 1, wherein the biological fluid sample comprises whole blood, and the analyte comprises glucose.

3. The method of claim 1, wherein the measuring step is performed at a fixed assay period point during the assay period, and wherein the magnitude of the assay current at the fixed assay period point correlates generally linearly with the concentration, of the analyte over a range of concentrations.

4. The method of claim 3, wherein the biological fluid sample comprises whole blood, the analyte comprises glucose, and the concentration range comprises from about 0 to about 600 mg/dL.

* * * * *